(12) United States Patent
Cheng

(10) Patent No.: US 6,801,648 B2
(45) Date of Patent: Oct. 5, 2004

(54) OPTICAL IMAGING SYSTEM WITH SYMMETRIC OPTICAL PROBE

(76) Inventor: Xuefeng Cheng, 1775 Milmont Dr. Apt. A212, Milpitas, CA (US) 95035

( * ) Notice: Subject to any disclaimer, the term of this patent is extended or adjusted under 35 U.S.C. 154(b) by 527 days.

(21) Appl. No.: 09/778,614

(22) Filed: Feb. 6, 2001

(65) Prior Publication Data

US 2002/0037095 A1 Mar. 28, 2002

Related U.S. Application Data

(60) Provisional application No. 60/223,074, filed on Aug. 4, 2000.

(51) Int. Cl.$^7$ ................................................. G06K 9/00
(52) U.S. Cl. ........................ 382/134; 600/431; 356/342
(58) Field of Search ................................ 382/128, 129, 382/130, 131, 132, 133, 134, 169; 600/476, 431, 310, 342, 473; 356/342; 250/227.11, 358.1; 206/427

(56) References Cited

U.S. PATENT DOCUMENTS

| | | | |
|---|---|---|---|
| 3,963,351 A | | 6/1976 | Chance et al. |
| 4,555,179 A | * | 11/1985 | Langerholc et al. ......... 356/342 |
| 4,810,875 A | * | 3/1989 | Wyatt ..................... 250/227.11 |
| 4,829,184 A | * | 5/1989 | Nelson et al. ............ 250/358.1 |
| 5,119,815 A | | 6/1992 | Chance |

(List continued on next page.)

OTHER PUBLICATIONS

Chance et al., 1998, "A novel method for fast imaging of brain function, non–invasively, with light,"*Optics Express* 2(10):411–423.

(List continued on next page.)

Primary Examiner—Jayanti K. Patel
Assistant Examiner—Seyed Azarian

(57) ABSTRACT

The present invention generally relates to optical probes of optical imaging systems and methods thereof for providing two-or three-dimensional images of spatial or temporal distribution of chromophores and/or their properties in a physiological medium. More particularly, the present invention relates to optical probes of optical imaging systems equipped with optical sensors such as wave sources and wave detectors which are disposed on scanning surfaces of the optical probes in a symmetric fashion. A typical optical probe of the present invention includes at least two wave sources (a first wave source and a second wave source) as well as at least two wave detectors (a first wave detector and a second wave detector), where the first wave source is disposed closer to the first wave detector than the second wave detector, and where the second wave source is disposed closer to the second wave detector than the first wave detector. More particularly, the foregoing wave sources and detectors are arranged so that a first near-distance between the first wave source and the first wave detector is substantially similar or identical to a second near-distance between the second wave source and the second wave detector, and that a first far-distance between the first wave source and the second wave detector is substantially identical or similar to a second far-distance between the second wave source and the first wave detector. The near-distance is preferably one half of the far-distance but may be longer or shorter than the far-distance. Each pair of one of the wave sources and one of the wave detectors is arranged to generate the output signal.

66 Claims, 10 Drawing Sheets

U.S. PATENT DOCUMENTS

| | | | |
|---|---|---|---|
| 5,137,355 A | * 8/1992 | Barbour et al. | 356/342 |
| 5,167,230 A | 12/1992 | Chance | |
| 5,402,778 A | 4/1995 | Chance | |
| 5,555,885 A | * 9/1996 | Chance | 600/431 |
| 5,564,417 A | 10/1996 | Chance | |
| 5,596,987 A | 1/1997 | Chance | |
| 5,664,574 A | * 9/1997 | Chance | 600/473 |
| 5,782,755 A | 7/1998 | Chance et al. | |
| 5,792,051 A | 8/1998 | Chance | |
| 5,807,263 A | 9/1998 | Chance | |
| 5,820,558 A | 10/1998 | Chance | |
| 5,835,617 A | 11/1998 | Ohta et al. | |
| 5,853,370 A | 12/1998 | Chance et al. | |
| 5,865,754 A | * 2/1999 | Sevick-Muraca et al. | 600/476 |
| 5,873,821 A | 2/1999 | Chance et al. | 600/407 |
| 5,899,865 A | 5/1999 | Chance | |
| 5,917,190 A | 6/1999 | Yodh et al. | |
| 5,954,053 A | 9/1999 | Chance et al. | |
| 5,987,351 A | 11/1999 | Chance | |
| 6,058,324 A | * 5/2000 | Chance | 600/473 |
| 6,134,460 A | * 10/2000 | Chance | 600/342 |
| 6,192,260 B1 | 2/2001 | Chance | |
| 6,227,367 B1 | * 5/2001 | Harrelson et al. | 206/427 |
| 6,272,367 B1 | 8/2001 | Chance | 600/407 |
| 6,304,771 B1 | * 10/2001 | Yodh et al. | 600/476 |

OTHER PUBLICATIONS

Cubeddu et al., 1998, "In vivo absorption and scattering spectra of human tissues in the red and near infrared," *TOPS 21*: 271–274.

Chance et al., "New Optical Probe Designs For Absolute (Self–Calibrating) NIR Tissue Hemoglobin Measurements" SPIE Conference on Optical Tomography and Spectroscopy of Tissue III, SPIE Vol 3597, Jan. 1999, pp 618–631.

Du et al., 1998, "Quantitative detection of hemoglobin saturation on piglet brain by near–infrared frequency–domain spectroscopy," *Proceedings of Photon Propagation in Tissues III (SPIE) 3194*: 55–62.

Fantini et al., 1999, "Non–invasive optical mapping of the piglet brain in real time," *Optics Express 4*(8):308–314.

Ma et al., "Quantitative study of hypoxia stress in piglet brain by IQ phase modulation oximetry," *Part of the SPIE Conference on Optical Tomography and Spectroscopy of Tissue III*, San Jose California. Jan. 1999. SPIE vol. 3597, pp. 642–649.

Pogue et al., 1997, "Instrumentation and design of a frequency–domain diffuse optical tomography imager for breast cancer detection," *Optics Express 1*(13):391–403.

Siegel et al., "Diffuse optical tomography of rat brain function," *Part of the SPIE Conference on Optical Tomography and Spectroscopy of Tissue III*, San Jose, California. Jan. 1999. SPIE vol. 3597, pp. 252–261.

* cited by examiner

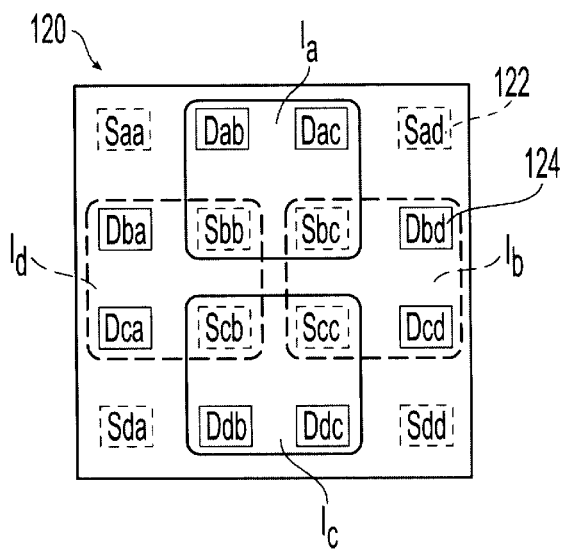
Fig. 5A
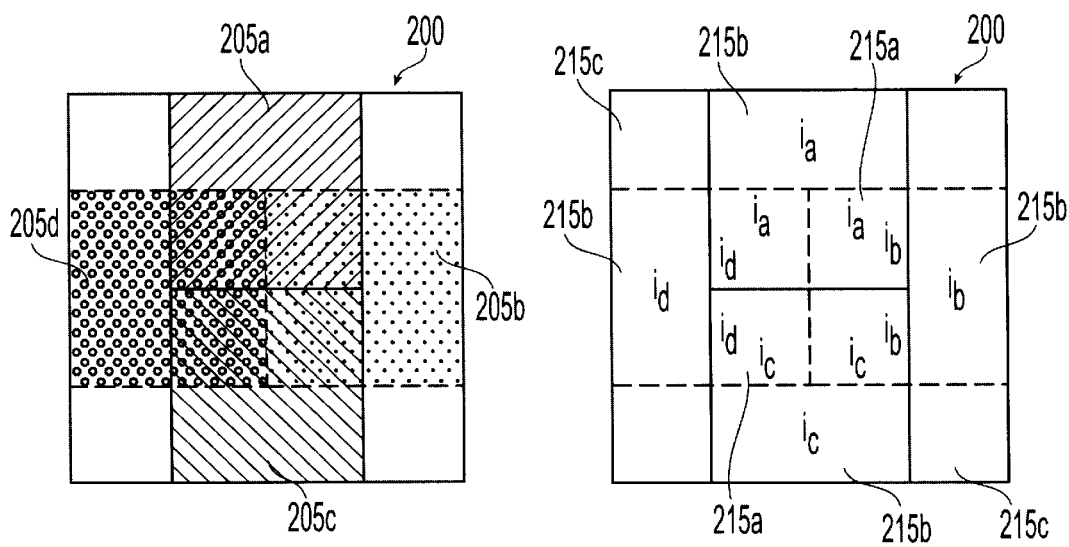
Fig. 5B
Fig. 5C

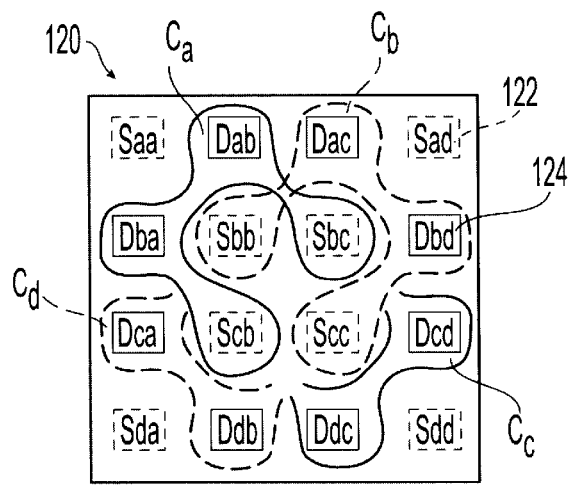
*Fig. 6A*
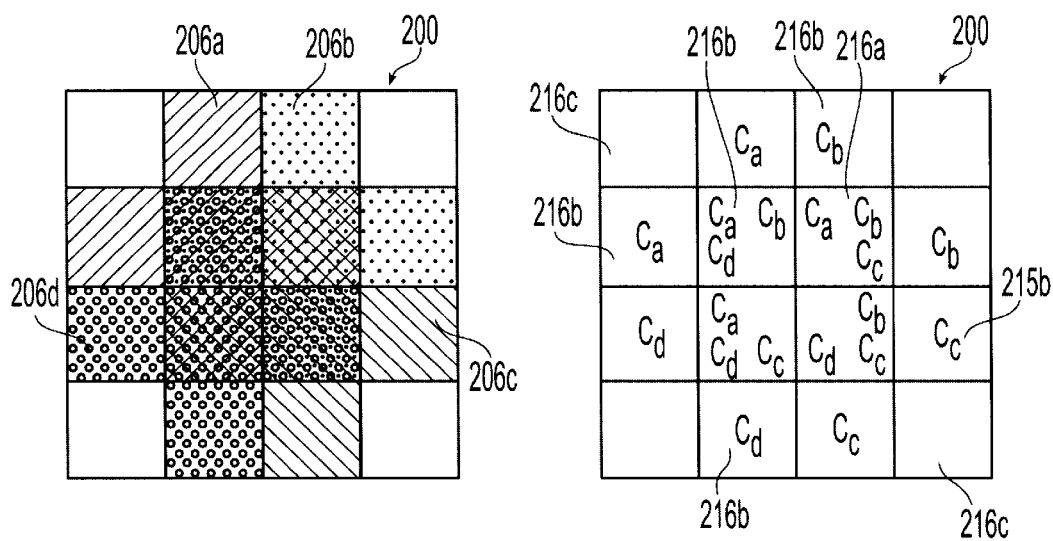
*Fig. 6B*  *Fig. 6C*

OPTICAL IMAGING SYSTEM WITH SYMMETRIC OPTICAL PROBE

CROSS-REFERENCE TO RELATED APPLICATIONS

This application claims the benefit of the filing date of U.S. Provisional Patent Application bearing Ser. No. 60/223,074, entitled "A Self-Calibrated Optical Scanner for Diffuse Optical Imaging" and filed on Aug. 4, 2000.

FIELD OF THE INVENTION

The present invention generally relates to optical imaging systems, optical probes thereof, and methods thereof for providing images of spatial or temporal distribution of chromophores or their properties in various physiological media. More particularly, the present invention relates to optical imaging systems and/or optical probes thereof including symmetrically arranged optical sensors such as wave sources and/or detectors. The present invention is applicable to any optical imaging systems and/or optical probes thereof whose operation is based on wave equations including the Beer-Lambert equation, modified Beer-Lambert equation, photon diffusion equation, and their equivalents.

BACKGROUND OF THE INVENTION

Near-infrared spectroscopy has been used to measure various physiological properties in animal and human subjects. The basic principle underlying the near-infrared spectroscopy is that a physiological medium such as tissues and cells includes a variety of light-absorbing and light-scattering chromophores which can interact with electromagnetic waves transmitted thereto and traveling therethrough. For example, human tissues include numerous chromophores among which deoxygenated and oxygenated hemoglobins are the most dominant chromophores in the spectrum range of 600 nm to 900 nm. Therefore, the near-infrared spectroscope has been applied to measure oxygen levels in the physiological medium in terms of tissue hemoglobin oxygen saturation ("oxygen saturation" hereinafter). Technical background for the near-infrared spectroscopy and diffuse optical imaging has been discussed in, e.g., Neuman, M. R., "Pulse Oximetry: Physical Principles, Technical Realization and Present Limitations," *Adv. Exp. Med. Biol.*, vol. 220, p.135–144, 1987, and Severinghaus, J. W., "History and Recent Developments in Pulse Oximetry," *Scan. J. Clin. and Lab. Investigations*, vol. 53, p.105–111, 1993.

Various techniques have been developed for the near-infrared spectroscopy, including time-resolved spectroscopy (TRS), phase modulation spectroscopy (PMS), and continuous wave spectroscopy (CWS). In a homogeneous, semi-infinite model, the TRS and PMS have generally been used to solve the photon diffusion equation, to obtain the spectra of absorption coefficients and reduced scattering coefficients of the physiological medium, and to estimate concentrations of the oxygenated and deoxygenated hemoglobins and oxygen saturation. The CWS has generally been used to solve the modified Beer-Lambert equation and to calculate changes in the concentrations of the oxygenated and deoxygenated hemoglobins.

Despite their capability of providing hemoglobin concentrations as well as the oxygen saturation, the major disadvantage of the TRS and PMS is that the equipment has to be bulky and, therefore, expensive. The CWS may be manufactured at a lower cost but is generally limited in its utility, for it can estimate only the changes in the hemoglobin concentrations but not the absolute values thereof. Accordingly, the CWS cannot provide the oxygen saturation. The prior art technology also requires a priori calibration of optical probes before their clinical application by, e.g., measuring a baseline in a reference medium or in a homogeneous portion of the medium. Furthermore, all prior art technology requires complicated image reconstruction algorithms to generate images of two-dimensional and/or three-dimensional distribution of the chromophores or their properties.

Accordingly, there exist needs for more efficient and reliable optical imaging systems and optical probes thereof for measuring absolute values of chromophores or their properties, for calibrating signals and images from such systems and probes while obviating the need for separate calibration procedure, and for constructing the images of the foregoing distribution of the chromophores or their properties on a substantially real time basis.

SUMMARY OF THE INVENTION

The present invention generally relates to optical imaging systems, optical probes thereof, and methods therefor (collectively referred to as "optical imaging system" or "optical probe" hereinafter) for providing two-dimensional or three-dimensional images of spatial or temporal distribution of chromophores or their properties in various physiological media. More particularly, the present invention relates to the optical imaging systems that are equipped with optical probes incorporating symmetrically arranged wave sources and wave detectors.

In one aspect of the invention, an optical imaging system is provided for generating images of a target area of a physiological medium, where the images represent two- and/or three-dimensional spatial and/or temporal distribution of the chromophores or their properties in the target area of the medium. Such an optical imaging system typically includes at least one wave source arranged to form optical coupling with the physiological medium and to irradiate electromagnetic waves into the medium and at least one wave detector arranged to detect electromagnetic waves from the medium and to generate output signal in response thereto. The optical imaging system then groups the wave sources and detectors such that each pair of one wave source and one wave detector forms a scanning element in which the wave source irradiates electromagnetic waves into the target area of the medium and in which the wave detector detects the electromagnetic waves irradiated by the wave source and generates the output signal in response thereto. The optical imaging system also groups the wave sources and detectors (or groups multiple scanning elements themselves) in order to define multiple symmetric scanning units each of which includes at least two wave sources and at least two wave detectors such as a first wave source, second wave source, first wave detector, and second wave detector. The first wave source may be disposed closer to the first wave detector than the second wave detector, while the second wave source is disposed closer to the second wave detector than the first wave detector. The wave sources and detectors are also arranged so that a first near-distance between the first wave source and first wave detector is identical or substantially similar to a second near-distance between the second wave source and second wave detector. In addition, a first far-distance between the first wave source and the second wave detector is identical or substantially similar to a second far-distance between the second wave source and the first wave detector. The near-distance is preferably about one half of the far-distance but may also be arranged to be longer or shorter than one half of the far-distance.

Embodiments of this aspect of the present invention includes one or more of the following features.

The symmetric scanning unit may include an axis of symmetry such that the first and second wave sources are disposed symmetric to such axis and the first and second wave detectors are also disposed symmetric thereto. Multiple symmetric scanning units may be arranged to include at least one common wave source and/or at least one common wave detector.

The wave sources and detectors of such scanning units may be substantially linearly disposed so that the wave sources (or detectors) are interposed between the wave detectors (or sources). Two or more symmetric scanning units may share the common axis of symmetry, e.g., where the first scanning unit has a first source-detector arrangement and where the second scanning unit is disposed below the first scanning unit and has the same first arrangement or, in the alternative, has a second source-detector arrangement which is different from or substantially reverse to the first source-detector arrangement. In one embodiment, four symmetric scanning units may be arranged to share the common axis of symmetry, e.g., where the first scanning unit has a first source-detector arrangement, where the second scanning unit is disposed below the first scanning unit and has a second source-detector arrangement substantially reverse to the first arrangement, where the third scanning unit is disposed below the second scanning unit and has the second arrangement, and where the fourth scanning unit is disposed below the third scanning unit and has the first source-detector arrangement. The foregoing scanning units may have identical shapes and sizes and define a 4×4 rectangular or square source-detector array so that adjacent wave sources and detectors are spaced apart by a uniform distance.

The wave sources and detectors may be disposed to form four vertices of a quadrangle, e.g., with the wave sources disposed at two upper vertices of the quadrangle while the wave detectors are disposed at two lower vertices thereof. Examples of such quadrangles include a square, rectangle, and trapezoid having two sides of equal lengths. Two or more of quadrangular scanning units may be arranged to have different sizes, to be disposed with respect to different axes of symmetry, and/or to have the same, different or reverse source-detector arrangements. Such quadrangular scanning units may be provided in various geometric arrangement, e.g., a side by side arrangement, stacked arrangement, arcuate arrangement or a combination thereof. For example, four quadrangular symmetric scanning units may be arranged so that the first scanning unit has a first source-detector arrangement, that the second scanning unit is disposed next to the first scanning unit and has a second source-detector arrangement which is substantially reverse to the first arrangement, that the third scanning unit is disposed below the first scanning unit and has the second arrangement, and that the fourth scanning unit is disposed below the second symmetric scanning unit and has the first arrangement. Alternatively, the first set of the wave sources and detectors may be substantially linearly disposed to define a linear scanning unit, while the second set of the wave sources and detectors may be disposed to form four vertices of such quadrangle and, therefore, to define an areal scanning unit. The first and second sets of the sensors may be arranged to include at least one common wave source and/or at least one common wave detector.

Alternatively, the symmetric scanning unit may include a point of symmetry so that the first and second wave sources are symmetrically disposed with respect to such point and the first and second wave detectors are also disposed symmetrically thereto. The symmetric scanning units may be arranged to include at least one common wave source and/or at least one common wave detector. The wave sources and detectors may also be substantially linearly disposed or may be disposed to form four vertices of a quadrangle, in which the first wave source and the first wave detector are disposed at two upper vertices of the quadrangle, while the second wave detector and the second wave source are disposed at two lower vertices thereof. Examples of such quadrangles may include, but not limited to, a rectangle and a parallelogram having two adjacent sides of different lengths (i.e., excluding a diamond-shaped parallelogram).

The symmetric scanning unit may also include one or more additional wave sources and/or detectors which may be disposed along a side, in a corner or in a middle portion of the scanning unit. In turn, the optical imaging system may include two or more symmetric scanning units arranged symmetrically with respect to a global axis of symmetry or a global point of symmetry in various arrangements, e.g., a side by side, stacked, angled, arcuate, and/or concentric arrangement. The symmetric scanning unit may also be arranged asymmetrically with respect to the other scanning units or to intersect and/or overlap other scanning units as well.

The wave sources may irradiate multiple sets of electromagnetic waves having different wave characteristics and the wave detectors may detect multiple sets of electromagnetic waves having different wave characteristics. In addition, the wave sources may be synchronized so that when one wave source is irradiating electromagnetic waves, other wave sources are turned off.

In another aspect of the invention, an optical imaging system includes four or more symmetric scanning units, where a first scanning unit is identical to a fourth scanning unit and where a second scanning unit is identical to a third scanning unit. Each symmetric scanning unit includes a first wave source, a second wave source, a first wave detector, and a second wave detector, where the first wave source is disposed closer to the first than the second wave detector and where the second wave source is disposed closer to the second than the first wave detector. The wave sources and detectors are arranged to render a first near-distance between the first wave source and first wave detector identical or substantially similar to a second near-distance between the second wave source and second wave detector and to render a first far-distance between the first wave source and second wave detector identical or substantially similar to a second far-distance between the second wave source and first wave detector. At least one of the first and second wave sources may be arranged to be synchronized with at least one of the first and second wave detectors so as to generate the output signals which represent optical interaction between the near-infrared waves and the hemoglobins in said target areas of said medium.

Embodiments of this aspect of the present invention includes one or more of the following features.

All wave sources and detectors of each scanning unit may be substantially linearly disposed. For example, the first and second wave sources (or detectors) may be interposed between the first and second wave detectors (or sources) in the first and fourth (or second and third) scanning units.

In yet another aspect of the present invention, an optical probe of an optical imaging system is provided to generate images representing distribution of chromophores or their properties in target areas of a physiological medium. Such an optical probe includes multiple wave sources and multiple wave detectors, where the wave sources are arranged to form optical coupling with the target areas of the medium and to irradiate electromagnetic waves thereinto, while the wave detectors are arranged to detect electromagnetic waves and to generate output signals in response thereto. In general, at least one first wave source and at least one first wave detector define a first scanning element in which the first wave source irradiates electromagnetic waves and in which the first wave detector detects such waves irradiated by the first wave detector and generates a first output signal. At least one second wave source and at least one second wave detector also define a second scanning element in which the second wave source irradiates electromagnetic waves and in which the second wave detector detects such waves irradiated by the second wave detector and generates a second output signal. The first and second scanning elements define a scanning unit in which the first and second wave sources are symmetrically disposed with respect to one of a line of symmetry and a point of symmetry and in each of which the first and second wave detectors are also symmetrically disposed with respect to one of the line of symmetry and the point of symmetry. Two or more of such scanning units may be arranged to intersect or overlap each other.

Embodiments of this aspect of the present invention includes one or more of the following features.

The optical probe may include an imaging member arranged to receive the first and second output signals generated by the first and second wave detectors, to obtain a set of solutions of multiple wave equations applied to the first and second wave sources and to the first and second wave detectors, to determine the distribution of the chromophores or their properties, and to generate the images of such distribution. Such images are generally provided in an image domain and are comprised of multiple voxels, where each of the first and second scanning units generates multiple first voxels as well as multiple second voxels, respectively. The imaging member is arranged to calculate at least one first voxel value for each of the first voxels from the set of solutions and at least one second voxel value for each of the second voxels from the same set of solutions. The imaging member is also arranged to define multiple cross-voxels each of which is defined as an overlapping portion of the first and second voxels intersecting each other.

The imaging member is also arranged to calculate at least one cross-voxel value for each of the cross-voxels directly from the first and second voxel values of the intersecting first and second voxels, respectively. Each of the cross-voxel values can be obtained as an arithmetic sum or arithmetic average of the first and second voxel values of the first and second voxels intersecting each other. Alternatively, each cross-voxel value may also be obtained at a weighted sum or weighted average of the first and second voxel values of the first and second voxels intersecting each other.

In a further aspect, a method is provided to generate the foregoing images of a target area of a physiological medium by an optical imaging system with an optical probe including the foregoing wave sources and detectors. The method generally includes the steps of providing multiple scanning elements each including at least one wave source for irradiating said waves and at least one wave detector for detecting such waves irradiated by the wave source of each of such scanning units, defining multiple scanning units each including at least two scanning elements and, therefore, each including at least two wave sources and detectors, scanning the target area by irradiating electromagnetic waves into such target area by the wave sources and by generating the output signals therefrom by the wave detectors, grouping such output signals generated by each scanning units, obtaining a set of solutions of wave equations applied to the wave sources and detectors of each of the scanning units, determining the distribution of the chromophores and/or properties thereof from the set of solutions, and providing the images of such distribution.

Embodiments of this aspect of the present invention includes one or more of the following features.

The method may include the steps of scanning said target area over a certain period of time, determining the distribution of the chromophores or properties thereof in the target area of the medium over time, providing the images of such distribution over time, and providing the images of changes in such distribution over time.

The method may also include the steps of defining a plurality of first voxels in at least one of the scanning units, determining at least one first voxel value for each of the first voxels, where each first voxel value represents an average value of the chromophores or their properties, generating the images of such distribution directly from the first voxel values. The method also includes the step of controlling resolution of the final images by adjusting at lease one characteristic dimension of each first voxel, e.g., by controlling the distance between the wave source and detector in one scanning element or unit, adjusting geometric arrangement between the wave source and wave detector in one scanning element or unit, adjusting geometric arrangement between multiple scanning elements in a scanning unit, adjusting geometric arrangement between at least two scanning units and adjusting a data sampling rate of the output signals.

The method may also include the steps of defining multiple second voxels in at least one scanning unit, determining at least one second voxel value for each second voxel where each second voxel value represents an average value of the chromophores or their properties, generating the images of such distribution directly from the first and second voxel values.

The method may include the steps of defining multiple cross-voxels in each scanning unit where the cross-voxel is defined as an overlapping portion of two or more intersecting first and second voxels, determining at least one cross-voxel value for each of the cross-voxels where each cross-voxel value is an average value of the chromophores or their properties, and generating the images of such distribution directly from the cross-voxel values, first voxel values, and second voxel values. The cross-voxel values are determined by, e.g., adding the first and second voxel values of the intersecting first and second voxels, arithmetically averaging the first and second voxel values of the intersecting first and second voxels, adding weighted first and second voxel values of the intersecting first and second voxels, and weight-averaging the first and second voxel values of the intersecting first and second voxels.

The method may also include the steps of defining multiple third voxels in the scanning units, determining one or more third voxel value for each of the third voxels where each third voxel value reflects an average value of at least one of the chromophores or their properties thereof, and generating the images of the distribution directly from the first, second, and third voxel values. In addition, the method may further include the steps of defining multiple second cross-voxels in the scanning units where each second cross-voxel is defined as an overlapping portion of two or more intersecting first and third voxels, determining at least one second cross-voxel value for each second cross-voxel where such second cross-voxel value reflects an average value of the chromophores or their properties, and generating the images of such distribution based on the cross-voxel values, second cross-voxel values, first voxel values, second voxel values, and third voxel values.

Each of the foregoing optical imaging systems and methods of the present invention may incorporate analytical and/or numerical solution schemes disclosed in the commonly assigned co-pending U.S. non-provisional patent application bearing Ser. No. 09/664,972, entitled "A system and Method for Absolute Oxygen Saturation" which has been filed on Sep. 18, 2000 by Xuefeng Cheng, Xiaorong Xu, Shuoming Zhou, and Ming Wang and which is incorporated herein by reference in its entirety (referred to as "the '972 application" hereinafter). Such optical imaging systems can calculate absolute values of concentration of oxygenated hemoglobin, [HbO], that of deoxygenated hemoglobin, [Hb], oxygen saturation, $SO_2$, and temporal changes in blood volume or water by adopting any of the schemes disclosed in the co-pending '972 application. Accordingly, such optical imaging systems provide the foregoing images of distribution of the chromophores and their properties that allow physicians to make direct diagnosis of the target area of the medium based on "absolute" or "relative" values thereof in the physiological media. It is noted that operational characteristics of the optical probes and optical imaging systems of the present invention incorporating any of the solution schemes disclosed in the above co-pending '972 application are only minimally affected by the number of wave sources and/or detectors and by geometric configuration therebetween. Therefore, unless otherwise specified, the optical imaging systems of the present invention may include any number of wave sources and/or detectors arranged in any geometric arrangements, subject to the "symmetry requirements" of the co-pending '972 application which will also be discussed in greater detail below.

As used herein, a "hemoglobin" or "hemoglobins" mean either or both of oxygenated hemoglobin and deoxygenated hemoglobin. The "hemoglobin," "hemoglobins" or "values of hemoglobins" represent properties of such "hemoglobins." Examples of such properties may include, but not limited to, amount or concentration thereof, total amount or concentration thereof (which corresponds to the sum of each amount or concentration of the oxygenated and deoxygenated hemoglobins), and the like.

"Chromophores" mean any substances in a physiological medium that can optically interact with electromagnetic waves transmitting therethrough. In general, such chromophore may include solvents of a medium, solutes dissolved in the medium, and/or other substances included in the medium. Specific examples of such chromophores may include, but not limited to, cytochromes, enzymes, hormones, neurotransmitters, chemo- or chemical transmitters, proteins, cholesterols, apoproteins, lipids, carbohydrates, cytosomes, blood cells, cytosols, water, hemoglobins, and other optical materials present in the animal or human cells, tissues or body fluid. Such "chromophores" may also include extra-cellular substances which may be injected into the medium for therapeutic and/or imaging purposes and may interact with electromagnetic waves. Such "chromophores" may include, but not limited to, dyes, contrast agents, and other image-enhancing agents, each of which may be designed to exhibit optical interaction with electromagnetic waves having wavelengths in a specific range.

"Electromagnetic waves" as used herein generally refer to acoustic or sound waves, near-infrared rays, infrared rays, visible light rays, ultraviolet rays, lasers, and/or rays of photons.

"Property" of the chromophores refers to intensive property, including their concentrations, a sum of such concentrations, a difference therebetween, and a ratio thereof. "Property" may also refer to extensive property such as, e.g., volume, mass, mass flow rate, weight, volume, and volumetric flow rate of the chromophores.

The term "value" is an absolute or relative value which represents spatial or temporal changes in the property of the chromophores.

"Distribution" means two-dimensional or three-dimensional distribution of the values of the chromophore or their properties. The "distribution" may be measured or estimated in a spatial, temporal, and/or image domains.

Unless otherwise defined, all technical and scientific terms used herein have the same meaning as commonly understood and/or used by one of ordinary skill in the art to which this invention belongs. Although methods and materials similar or equivalent to those described herein can be applied and/or used in the practice of or testing the present invention, suitable methods and materials are described below. All publications, patent applications, patents, and other references mentioned herein are incorporated by reference in their entirety. In case of conflict, the present application, including definitions, will control. In addition, the materials, methods, and examples are illustrative only and not intended to be limiting.

Other features and advantages of the invention will be apparent from the following detailed description and from the appended claims.

BRIEF DESCRIPTION OF THE DRAWINGS

FIG. 5A is a schematic diagram of a second set of scanning units of the optical probe of FIG. 1A according to the present invention;

FIG. 5B is a schematic diagram of voxels and cross-voxels generated by the scanning units of FIG. 5A according to the present invention;

FIG. 5C is a schematic diagram of resulting voxel values and cross-voxel values of FIG. 5B according to the present invention;

FIG. 6A is a schematic diagram of a third set of scanning units of the optical probe of FIG. 1A according to the present invention;

FIG. 6B is a schematic diagram of voxels and cross-voxels generated by the scanning units of FIG. 6A according to the present invention;

FIG. 6C is a schematic diagram of voxel values and cross-voxel values of FIG. 6B according to the present invention;

DETAILED DESCRIPTION OF THE INVENTION

The following description provides source-detector arrangements or sensor arrangements for optical probes, optical imaging systems, and methods therefor to provide images of two- and/or three-dimensional spatial or temporal distribution of chromophores and/or their properties in a target area of various physiological media. More particularly, the following description provides preferred aspects and embodiments of symmetric sensor arrangements for optical probes of the optical imaging systems.

In one aspect of the present invention, an optical imaging system includes an optical probe having symmetrically arranged optical sensors (i.e., wave sources and wave detectors) for generating images of spatial or temporal distribution of the chromophores and/or their properties in the target area of the physiological medium.

Figure 1A:
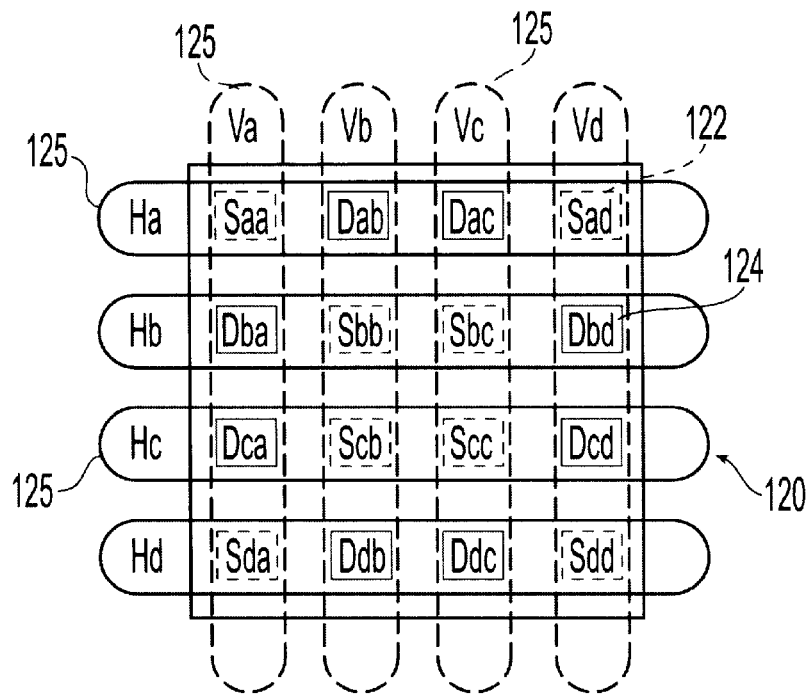
FIG. 1A is a schematic diagram of an optical probe of an optical imaging system defining multiple scanning units according to the present invention.

FIG. 1A is a schematic diagram of an optical probe of an optical imaging system having multiple scanning units according to the present invention. An exemplary optical imaging system includes an optical probe 120 including eight wave sources 122 (e.g., $S_{aa}$, $S_{ad}$, $S_{bb}$, $S_{bc}$, $S_{cb}$, $S_{cc}$, $S_{da}$, and $S_{dd}$) and eight wave detectors 124 (e.g., $D_{ab}$, $D_{ac}$, $D_{ba}$, $D_{bd}$, $D_{ca}$, $D_{cd}$, $D_{db}$, and $D_{dc}$) where optical sensors (i.e., wave sources 122 and detectors 124) are disposed on a scanning surface thereof. In general, each pair of wave source 122 and detector 124 forms a scanning element which forms a basic functional unit of optical probe 120. In each scanning element, wave source 122 irradiates electromagnetic waves into the target area of the medium and wave detector 124 detects such electromagnetic waves which have interacted with (e.g., absorbed and/or scattered) and which emanate from the target area of the medium and then generates an output value which represents an amplitude of the electromagnetic waves detected thereby across the scanning element.

Instead of directly using the output values generated by each of the scanning elements, one or more wave sources 122 and/or detectors 124 are preferably grouped to further define a "sensor assembly," "sensor array" or "scanning unit" 125, where one or more wave detectors 124 of each scanning unit 125 are arranged to detect electromagnetic waves irradiated by one or more wave sources 122 of the same scanning unit so that an area of the medium (referred to as a "target area" hereinafter) can be scanned by the scanning unit 125. Thus, each scanning unit 125 can generate an output signal which is a collection of multiple output values each of which is generated by multiple scanning elements of the same scanning unit.

Each scanning unit 125 is generally defined around its optical sensors 122, 124 and arranged to form an uninterrupted scanning area so that the optical property of a particular target area can be obtained by a single scanning of the medium by optical probe 120. It is noted in the figure that the end portions of scanning units 125 are elongated only for illustration purposes. Configuration of scanning unit 125 and scanning area thereof is generally determined by that of the source-detector arrangement such as, e.g., the number of wave sources 122 and detectors 124 in each scanning unit 125, grouping or pairing of wave sources 122 and detectors 124 in each scanning element, grouping or pairing of the scanning elements in each scanning unit 125, geometric arrangement between sensors 122, 124, that between the scanning elements of each scanning unit 125, that between scanning units 125 of the optical probes, irradiation capacity or emission power of wave sources 122, detection sensitivity of wave detectors 124, and the like.

Foregoing wave sources 122 are arranged to form optical coupling with the target area of the medium such that a sufficient amount of electromagnetic waves can be irradiated thereinto. Any conventional wave sources may be used in the optical probes of the present invention as long as they can irradiate or emit electromagnetic waves having preselected wavelengths, e.g., in the ranges from 100 nm to 5,000 nm, from 300 nm to 3,000 nm or, more particularly, in the "near-infrared" range from 500 nm to 2,500 nm. As will be described in greater detail below, however, wave sources are preferably arranged to irradiate near-infrared electromagnetic waves having wavelengths about 650 nm to 730 nm, e.g., 690 nm, and about 790 nm to 870 nm, e.g., 830 nm. The wave sources may emit or irradiate electromagnetic waves having different wave characteristics such as, e.g., different wavelengths, phase angles, frequencies, amplitudes, harmonics, etc. In the alternative, wave sources 122 may also irradiate electromagnetic waves in which identical, similar or different signal waves are superposed onto carrier waves which, in turn, have identical, similar or different wavelengths, frequencies, phase angles, amplitudes or harmonics. Each wave source 122 may also be fabricated to include multiple wave generators or optical pathways (e.g., multiple optical fibers for transmitting such electromagnetic waves therethrough) so that the electromagnetic waves having different wave characteristics are irradiated and/or transmitted therethrough. In the embodiment of FIG. 1, each of eight wave sources 122 is preferably arranged to irradiate or emit the "near-infrared" electromagnetic waves having two specific wave lengths, e.g., about 690 nm and about 830 nm.

Similarly, foregoing wave detectors 124 are also arranged to form optical coupling with the target area of the medium, to detect electromagnetic waves irradiated by foregoing wave sources 122 and transmitted therethrough, and to generate output signals in response to the amount of the electromagnetic waves detected thereby. Any conventional wave detectors may be used in the optical probe of the present invention so long as they have sensitivity to detect the electromagnetic waves having wavelengths in the foregoing ranges. Multiple wave detectors may be used to detect multiple sets of electromagnetic waves irradiated by different wave sources or such electromagnetic waves having non-identical wave characteristics. Multiple wave detectors may also generate multiple sets of output signals accordingly. Alternatively, a single wave detector may be arranged to detect multiple sets of electromagnetic waves and/or to generate multiple sets of output signals.

Selection of an optimal distance between the wave source and detector of each scanning element and scanning unit is generally a matter of choice of one of ordinary skill in the art. Such distance is generally determined by several factors including, but not limited to, optical properties of the medium (e.g., absorption and/or scattering coefficient thereof), irradiation or emission capacity of the wave sources, detection sensitivity of the wave detectors, and the like. In addition, operational characteristics of such optical probes are generally determined by the number of wave sources and/or detectors in each scanning element and each scanning unit, grouping or pairing of the wave sources and detectors in each scanning element and each scanning unit, geometric arrangement between the wave sources and detectors in each scanning element and between the scanning elements in each scanning unit, geometric arrangement of multiple scanning units in the optical probe, etc. It is preferred, however, that the distances between neighboring wave sources and detectors do not exceed the threshold sensitivity ranges of the wave detectors which may typically range from, e.g., several cm to 10 cm or, more particularly, about 5 cm for most human or animal tissues, cells or body fluids.

Still referring to FIG. 1A, foregoing optical sensors 122, 124 are arranged to form a 4-by-4 sensor array on the scanning surface of optical probe 120. Each row of the sensor array typically includes at least two wave sources 122 and at least two wave detectors 124 and forms a horizontally elongated scanning unit (e.g., $H_a$, $H_b$, $H_c$, and $H_d$). Similarly, each column of the sensor array includes two wave sources 122 and two wave detectors 124 and defines a vertically elongated scanning unit (e.g., $V_a$, $V_b$, $V_c$, and $V_d$). For example, in the first and fourth horizontal scanning units ($H_a$, $H_d$), two wave detectors $D_{ab}$-$D_{ac}$ and $D_{db}$-$D_{dc}$ are interposed between two wave sources $S_{aa}$-$S_{ad}$ and $S_{da}$-$S_{dd}$, respectively. Whereas, in the second and third horizontal scanning units ($H_b$, $H_c$), two wave sources $S_{bb}$-$S_{bc}$ and $S_{cb}$-$S_{cc}$ are interposed between two wave detectors $D_{ba}$-$D_{bd}$ and $D_{ca}$-$D_{cd}$, respectively. In addition, in the first and fourth vertical scanning units ($V_a$, $V_d$), two wave detectors $D_{ba}$-$D_{ca}$ and $D_{bd}$-$D_{cd}$ are interposed between two wave sources $S_{aa}$-$S_{da}$ and $S_{ad}$-$S_{dd}$, respectively, whereas, in the second and third vertical scanning units ($V_b$, $V_c$), two wave sources $S_{bb}$-$S_{cb}$ and $S_{bc}$-$S_{cc}$ are interposed between two wave detectors $D_{ab}$-$D_{db}$ and $D_{ac}$-$D_{dc}$, respectively.

Figure 1B:
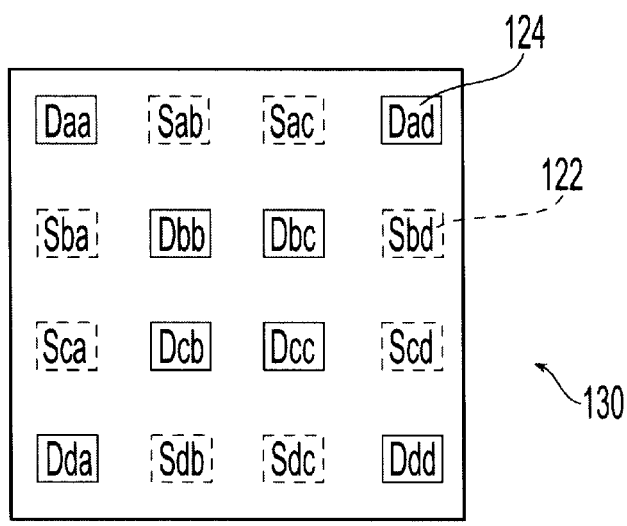
FIG. 1B is a schematic diagram of an optical probe of an optical imaging system defining multiple scanning units having a source-detector arrangement which is reverse to that of FIG. 1A according to the present invention.

The optical probes of the present invention may be provided with source-detector arrangements which are different from the one shown in FIG. 1A. For example, FIG. 1B is a schematic diagram of another optical probe of an optical imaging system according to the present invention. Similar to the one of FIG. 1A, this exemplary optical probe 130 also includes eight wave sources 122 (e.g., $S_{ab}$, $S_{ac}$, $S_{ba}$, $S_{bd}$, $S_{ca}$, $S_{cd}$, $S_{db}$, and $S_{dc}$) and eight wave detectors 124 (e.g., $D_{aa}$, $D_{ad}$, $D_{bb}$, $D_{bc}$, $D_{cb}$, $D_{cc}$, $D_{da}$, and $D_{dd}$) forming another 4×4 sensor array. However, optical sensors 122, 124 are provided in an arrangement which is completely reverse to that of FIG. 1A. That is, the wave sources of FIG. 1A are replaced by the wave detectors in FIG. 1B, while the wave detectors of FIG. 1A are substituted by the wave sources in FIG. 1B. As will be discussed in greater below, both optical probes 120, 130 can provide identical or at least substantially comparable performance characteristics.

It is preferred that, in each scanning unit 125 of optical probes 120, 130, a first wave source be disposed closer to a first wave detector than a second wave detector, and a second wave source be disposed closer to a second wave detector than a first wave detector. In addition, such wave sources and detectors are preferably arranged such that a first near-distance between the first wave source and the first wave detector be identical or substantially similar to a second near-distance between the second wave source and the second wave detector, and that a first far-distance between the first wave source and the second wave detector be identical or substantially similar to a second far-distance between the second wave source and the first wave detector. In the second horizontal scanning unit, $H_b$, e.g., the first wave source ($S_{bb}$) is disposed closer to the first wave detector ($D_{ba}$), and the second wave source ($S_{bc}$) closer to the second wave detector ($D_{bd}$) In addition, the first near-distance between the first wave source ($S_{bb}$) and the first wave detector ($D_{ba}$) can be arranged to be identical to the second near-distance between the second wave source ($S_{bc}$) and the second wave detector ($D_{bd}$). Furthermore, the first far-distance between the first wave source ($S_{bb}$) and the second wave detector ($D_{bd}$) is also arranged to be identical to the second far-distance between the second wave source ($S_{bc}$) and the first wave detector ($D_{ba}$).

As described in the co-pending '972 application, the foregoing symmetric arrangements of wave sources 122 and detectors 124 offer numerous advantages over the conventional optical imaging systems. First of all, the optical imaging system and optical probe of the present invention equipped with such symmetric arrangements enable direct estimation of the absolute values of concentration of deoxygenated hemoglobin, [Hb], that of oxygenated hemoglobin, [HbO], and oxygen saturation, $SO_2$. For example, such values can be obtained by the following equations (1a) to (1e) each of which corresponds to the equations (8a) to (8d) and (9b) of the co-pending '972 application, respectively:

$$[Hb] = \frac{\varepsilon_{HbO}^{\lambda_2} \frac{OD^{\lambda_1}}{F^{\lambda_1}} - \varepsilon_{HbO}^{\lambda_1} \frac{OD^{\lambda_2}}{F^{\lambda_2}}}{\varepsilon_{Hb}^{\lambda_1}\varepsilon_{HbO}^{\lambda_2} - \varepsilon_{Hb}^{\lambda_2}\varepsilon_{HbO}^{\lambda_1}} \quad (1a)$$

$$[HbO] = \frac{\varepsilon_{Hb}^{\lambda_1} \frac{OD^{\lambda_2}}{F^{\lambda_2}} - \varepsilon_{Hb}^{\lambda_2} \frac{OD^{\lambda_1}}{F^{\lambda_1}}}{\varepsilon_{Hb}^{\lambda_1}\varepsilon_{HbO}^{\lambda_2} - \varepsilon_{Hb}^{\lambda_2}\varepsilon_{HbO}^{\lambda_1}} \quad (1b)$$

$$F^{\lambda_1} = (B_{S1D2}{}^{\lambda_1} L_{S1D2} - B_{S1D1}{}^{\lambda_1} L_{S1D1}) + (B_{S2D1}{}^{\lambda_1} L_{S2D1} - B_{S2D2}{}^{\lambda_1} L_{S2D2}) \quad (1c)$$

$$F^{\lambda_2} = (B_{S1D2}{}^{\lambda_2} L_{S1D2} - B_{S1D1}{}^{\lambda_2} L_{S1D1}) + (B_{S2D1}{}^{\lambda_2} L_{S2D1} - B_{S2D2}{}^{\lambda_2} L_{S2D2}) \quad (1d)$$

$$SO_2 = \frac{\varepsilon_{Hb}^{\lambda_1} \frac{OD^{\lambda_2}}{OD^{\lambda_1}} \frac{F^{\lambda_1}}{F^{\lambda_2}} - \varepsilon_{Hb}^{\lambda_2}}{(\varepsilon_{Hb}^{\lambda_1} - \varepsilon_{HbO}^{\lambda_1})\frac{OD^{\lambda_2}}{OD^{\lambda_1}}\frac{F^{\lambda_1}}{F^{\lambda_2}} + (\varepsilon_{HbO}^{\lambda_2} - \varepsilon_{Hb}^{\lambda_2})} \quad (1e)$$

where the parameters "$\varepsilon_{Hb}$" and "$\varepsilon_{HbO}$" represent extinction coefficients of the deoxygenated and oxygenated hemoglobins, respectively, the variable "OD" is an optical density defined as a logarithmic ratio of light intensities (i.e., magnitudes or amplitudes of electromagnetic waves) detected by a wave detector, the parameter "B" is conventionally known as a "path length factor," the parameter "$L_{S1Dj}$" is a distance between an i-th wave source and a j-th wave detector, and the superscripts "$\lambda_1$" and "$\lambda_2$" represent that a parameter or variable is obtained by irradiating electromagnetic waves having wavelengths $\lambda_1$ and $\lambda_2$, respectively.

In the alternative, the foregoing absolute values may also be obtained by the over-determined iterative method as disclosed in the foregoing '972 application, where the absolute values of [Hb], [HbO], and $SO_2$ are determined by the following equations (2a) to (2c), each corresponding to the equations (17a) to (17c) of the co-pending '972 application, respectively:

$$[Hb] = \frac{\varepsilon_{HbO}^{\lambda_2} \mu_a^{\lambda_1} - \varepsilon_{HbO}^{\lambda_1} \mu_a^{\lambda_2}}{\varepsilon_{Hb}^{\lambda_1}\varepsilon_{HbO}^{\lambda_2} - \varepsilon_{Hb}^{\lambda_2}\varepsilon_{HbO}^{\lambda_1}} \quad (2a)$$

$$[HbO] = \frac{\varepsilon_{Hb}^{\lambda_1} \mu_a^{\lambda_2} - \varepsilon_{Hb}^{\lambda_2} \mu_a^{\lambda_1}}{\varepsilon_{Hb}^{\lambda_1}\varepsilon_{HbO}^{\lambda_2} - \varepsilon_{Hb}^{\lambda_2}\varepsilon_{HbO}^{\lambda_1}} \quad (2b)$$

$$SO_2 = \frac{[HbO]}{[Hb] + [HbO]}$$

$$= \frac{\varepsilon_{Hb}^{\lambda_1} \mu_a^{\lambda_2} - \varepsilon_{Hb}^{\lambda_2} \mu_a^{\lambda_1}}{(\varepsilon_{HbO}^{\lambda_2} \mu_a^{\lambda_1} - \varepsilon_{HbO}^{\lambda_1} \mu_a^{\lambda_2}) + (\varepsilon_{Hb}^{\lambda_1} \mu_a^{\lambda_2} - \varepsilon_{Hb}^{\lambda_2} \mu_a^{\lambda_1})} \quad (2c)$$

where the parameter "$\mu_a$" denotes an absorption coefficient of the medium. It is noted that an imaging member of the optical imaging system of the present invention may be arranged to receive output signals generated by the wave detectors and to calculate optical densities (defined below). Once the absolute values or their changes in the hemoglobin properties are determined, the imaging member generates images representing two- or three-dimensional spatial and/or temporal distributions of the hemoglobins by employing a real-time image constructing scheme which is discussed in another commonly assigned co-pending U.S. patent application bearing Ser. No. 09/778,617, entitled "Optical Imaging System for Direct Image Construction" which has been filed by Xiaorong Xu, Xuefeng Cheng, Shuoming Zhou, Lai Wang, and Ming Wang on Dec. 30, 2000 and which is incorporated herein in its entirety by reference.

In the alternative, changes in the distribution of the hemoglobins and/or their properties may be determined by estimating changes in the optical characteristics of the target area of the medium. For example, changes in the concentrations of oxygenated and deoxygenated hemoglobins may be calculated by assessing differences in their extinction coefficients measured by employing electromagnetic waves with different wavelengths. In an exemplary numerical scheme, the photon diffusion equations are modified and solved by employing diffusion approximation described in Keijer et al., "Optical Diffusion in Layered Media," *Applied Optics*, vol. 27, p. 1820–1824 (1988) and also in Haskell et al., "boundary Conditions for Diffusion Equation in Radiative Transfer," *Journal of Optical Society of America, A*, vol. 11, p.2727–2741, 1994:

$$\begin{bmatrix} \Phi_{SC}(r_{S1}, r_{D1}) \\ \vdots \\ \Phi_{SC}(r_{SM}, r_{DM}) \end{bmatrix}_{M,1} = \begin{bmatrix} W_{11} & \cdots & W_{1N} \\ \vdots & \ddots & \vdots \\ W_{M1} & \cdots & W_{MN} \end{bmatrix}_{M,N} \cdot \begin{bmatrix} \Delta\mu_{a,1} \\ \vdots \\ \Delta\mu_{a,N} \end{bmatrix}_{N,1} \quad (3)$$

where the symbol "$\Phi_{SC}(r_{S1}, r_{Dj})$" represents a normalized optical density measured by a j-th wave detector in response to an i-th wave source, the variables "$r_{Si}$" and "$r_{Dj}$" are positions of the i-th wave source and j-th wave detector, respectively, the symbol "$\Delta\mu_{aj}$" denotes tissue optical perturbation, such as the changes in the absorption coefficient in an i-th voxel, the parameters "M" and "N" represent the number of measurements and the voxel number to be reconstructed, respectively, and the variable "$W_{ij}$" is a weight function which represents the probability that a photon travels from the i-th wave source to a certain point inside the target area of the medium and is then detected by the j-th wave detector. The weight function, $W_{1j}$, of equation (3) is defined as:

$$W_{ij} = \frac{G(r_{Di}, r_j) \cdot \Phi_0(r_{Si}, r_j) \cdot v \cdot h^3}{D_{photon}} \quad (4)$$

where the parameter "$h^3$" is the volume of a voxel, "$D_{photon}$" represents a photon diffusion coefficient, and "v" denotes the velocity of light in the physiological medium. In addition, the variable "$\Phi SC(r_{Si}, r_{Dj})$" represents a normalized optical density defined as:

$$\Phi_{SC}(r_{Si}, r_{Dj}) = \frac{I_B - I}{I_B} \quad (5)$$

where the variable "I" denotes an output signal measured by the sensor assembly comprised of the i-th wave source and j-th wave detector which are disposed in positions "$r_{Si}$" and "$r_{Dj}$," respectively, and the variable "$I_B$" denotes a baseline of the output signal detected by the wave detector.

Various methods such as, e.g., the direct matrix inversion and simultaneous iterative reconstruction techniques, may be applied to solve the above set of equations (3) to (5). Once the tissue optical perturbations, "$\Delta\mu_a^{\lambda_1}$" and "$\Delta\mu_a^{\lambda_2}$" are estimated by employing two wavelengths, $\lambda_1$ and $\lambda_2$, respectively, changes in the concentrations of the oxygenated and deoxygenated hemoglobins can be obtained as follows:

$$\Delta[Hb] = \frac{\varepsilon_{HbO}^{\lambda_2} \cdot \Delta\mu_a^{\lambda_1} - \varepsilon_{HbO}^{\lambda_1} \cdot \Delta\mu_a^{\lambda_2}}{\left(\varepsilon_{Hb}^{\lambda_1}\varepsilon_{HbO}^{\lambda_2} - \varepsilon_{HbO}^{\lambda_1}\varepsilon_{Hb}^{\lambda_2}\right) \cdot L} \quad (6a)$$

$$\Delta[HbO] = \frac{\varepsilon_{Hb}^{\lambda_1} \cdot \Delta\mu_a^{\lambda_2} - \varepsilon_{Hb}^{\lambda_2} \cdot \Delta\mu_a^{\lambda_1}}{\left(\varepsilon_{Hb}^{\lambda_1}\varepsilon_{HbO}^{\lambda_2} - \varepsilon_{Hb}^{\lambda_2}\varepsilon_{HbO}^{\lambda_1}\right) \cdot L} \quad (6b)$$

where L is the distance between the wave source and detector and the parameters $\varepsilon_{Hb}^{\lambda_1}$, $\varepsilon_{Hb}^{\lambda_2}$H, $\varepsilon_{HbO}^{\lambda_1}$, and $\varepsilon_{HbO}^{\lambda_2}$ refer to extinction coefficients of oxygenated hemoglobin and deoxygenated hemoglobin at two different wavelengths, $\lambda_1$ and $\lambda_2$, respectively.

Incorporating any of the foregoing solution schemes into the optical probes with the foregoing symmetric source-detector arrangements of the present invention offers further benefits over the prior art technology. Contrary to the CWS technology allowing measurement of changes in the hemoglobin concentrations, the symmetric source-detector arrangements described herein provide a direct means for assessing spatial and/or temporal distribution of the "absolute values" of various chromophore properties of the physiological medium, including those of hemoglobins. This also allows a physician to directly assess the oxygen concentrations and oxygen saturation in tissues, cells, organs, muscles or blood of an animal and/or human subject. The foregoing symmetric source-detector arrangements also allow the physician to make direct diagnosis of the test subject based on the "absolute values" of the chromophore properties of the medium thereof.

The scanning units of the optical probes of the present invention can adopt various source-detector arrangements which satisfy the symmetric requirements of the co-pending '972 application. FIGS. 2 and 3 are examples of such symmetric scanning units, where the wave sources and detectors are arranged symmetrically in FIGS. 2A to 2H with respect to a line of symmetry 127, whereas those are arranged symmetrically with respect to a point of symmetry 128 in FIGS. 3A to 3C. It is appreciated in the foregoing figures that the shapes and sizes of the wave sources and detectors are simplified and exaggerated for ease of illustration.

Figure 2A:
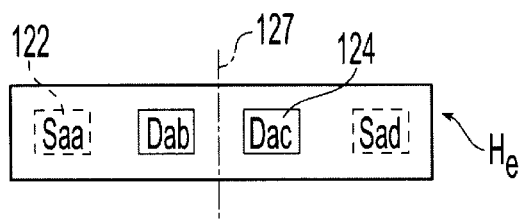
FIG. 2A is a schematic diagram of a linear scanning unit according to the present invention.
Figure 2H:
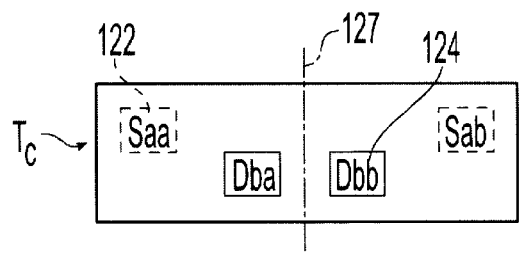
FIG. 2H is a schematic diagram of another trapezoidal scanning unit having an inverted source-detector arrangement according to the present invention.
Figure 2B:
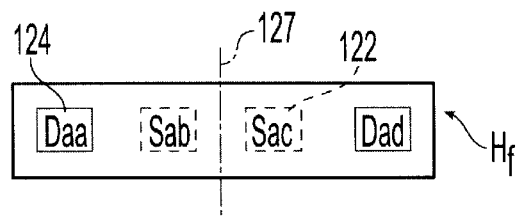
FIG. 2B is a schematic diagram of another linear scanning unit having a source-detector arrangement which is reverse to that of FIG. 2A according to the present invention.
Figure 3A:
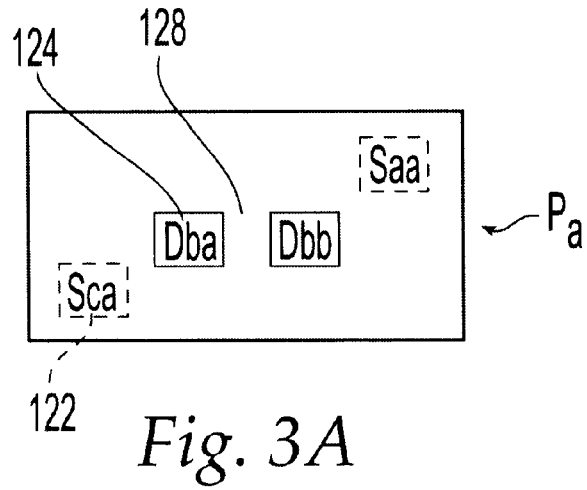
FIG. 3A is a schematic diagram of a quasi-linear scanning unit according to the present invention.
Figure 3B:
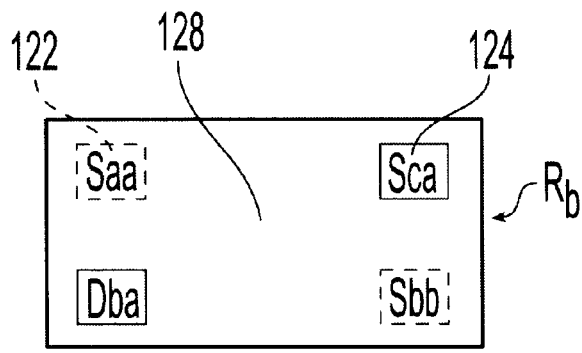
FIG. 3B is a schematic diagram of a rectangular scanning unit according to the present invention.
Figure 3C:
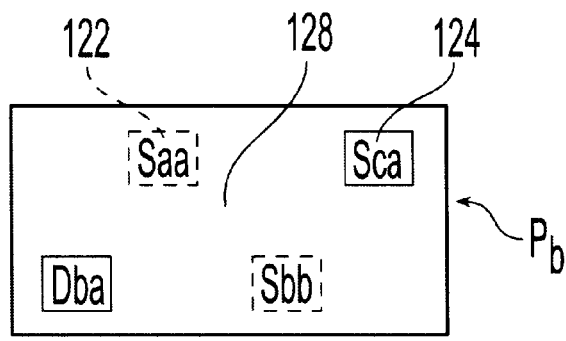
FIG. 3C is a schematic diagram of a parallelogram scanning unit according to the present invention.

FIGS. 2A and 2B are schematic diagrams of linear scanning units according to the present invention. The scanning units ($H_e$ and $H_f$) of FIGS. 2A and 2B are identical or substantially similar to those of FIGS. 1A and 1B and, therefore, automatically satisfy the symmetry requirements of the identical near- and far-distances between wave sources 122 and detectors 124. It is appreciated that such scanning unit ($H_e$ and $H_f$) can be modified without violating the foregoing symmetry requirements of the co-pending '972 application. For example, in the scanning unit, $H_e$, the distance between the neighboring wave source and detector may be lengthened or shortened as long as such distance does not exceed the threshold sensitivity range of the wave detector which may range from, e.g., several cm to 10 cm or, in particular, about 5 cm for most human and/or animal tissues. In addition, so long as the symmetry with respect to line of symmetry 127 can be maintained, the distance between wave detectors, $D_{ab}$ and $D_{ac}$, may also be adjusted to be identical to or different from the near-distances between the adjacent wave source and detector pairs such as $S_{aa}$-$D_{ab}$ and $D_{ac}$-$S_{ad}$.

Figure 2F:
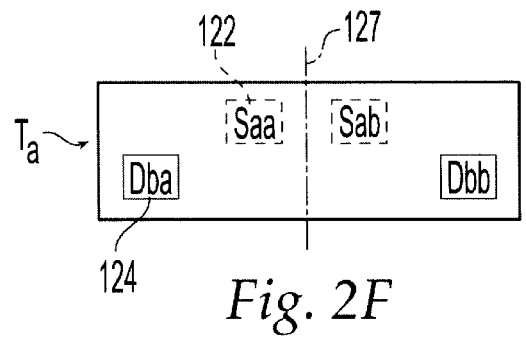
FIG. 2F is a schematic diagram of a trapezoidal scanning unit according to the present invention.
Figure 2C:
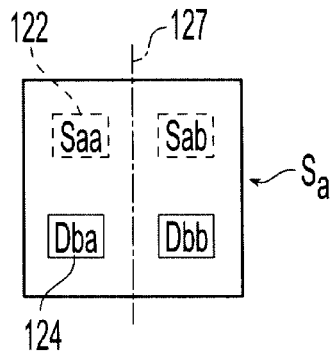
FIG. 2C is a schematic diagram of a square scanning unit according to the present invention.
Figure 2E:
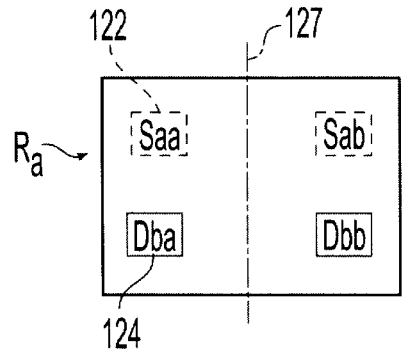
FIG. 2E is a schematic diagram of a rectangular scanning unit according to the present invention.
Figure 2D:
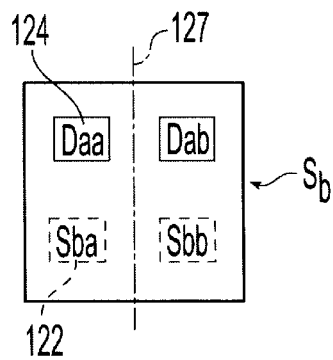
FIG. 2D is a schematic diagram of another square scanning unit having a source-detector arrangement which is reverse to that of FIG. 2C according to the present invention.

FIGS. 2C and 2D are schematic diagrams of square scanning units according to the present invention. In each of the square scanning units, two wave sources and two wave detectors are disposed at four vertices of the square. In particular, as shown in the scanning unit, $S_a$, two wave sources, $S_{aa}$ and $S_{ab}$, are disposed at the upper vertices of the square, two wave detectors, $D_{ba}$ and $D_{bb}$, are disposed at the lower vertices thereof, and line of symmetry 127 vertically passes through the middle of the square. Accordingly, the near-distance between the adjacent wave source and detector corresponds to the vertical distance between the wave source $S_{aa}$ (or $S_{ab}$) and detector $D_{ba}$ (or $D_{bb}$), while the far-distance is the diagonal length connecting the wave source $S_{aa}$ (or $S_{ab}$) and detector $D_{bb}$ (or $D_{ab}$). The same applies to the scanning unit, $S_b$, of FIG. 2D that has the source-detector arrangement which is reverse to that in FIG. 2C. As discussed above, both the near- or far-distance between the adjacent sensors may also be adjusted as long as the aforementioned sensitivity limitation is met by the wave detectors, $D_{aa}$ and $D_{ab}$.

FIG. 2E is a schematic diagram of a rectangular scanning unit according to the present invention, where two wave sources and two wave detectors are disposed at four vertices of the rectangular scanning unit, $R_a$. Similar to the foregoing scanning units, the source-detector arrangement of the foregoing scanning unit may also be reversed such that the wave sources are positioned at the upper vertices of the rectangle, whereas the wave detectors are arranged at the lower vertices thereof. The horizontal and vertical distances between the adjacent optical sensors may further be increased or decreased as long as the foregoing sensitivity limitation of the wave detectors is met.

Figure 2G:
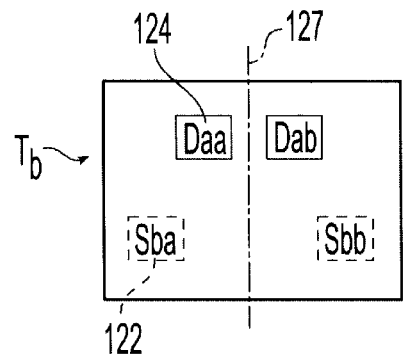
FIG. 2G is a schematic diagram of another trapezoidal scanning unit having a source-detector arrangement reverse to that of FIG. 2F according to the present invention.

FIGS. 2F and 2G represent schematic diagrams of trapezoidal scanning units according to the present invention. In the exemplary trapezoidal scanning unit, $T_a$, of FIG. 2F, two wave sources, $S_{aa}$ and $S_{ab}$, are disposed in the upper vertices of the trapezoid, while two wave detectors, $D_{ba}$ and $D_{bb}$, are disposed in the lower vertices thereof so that line of symmetry 127 passes through the middle of the trapezoid. More particularly, two opposing sides of the trapezoid are preferably arranged to have the same lengths so as to satisfy the foregoing symmetry requirements of the co-pending '972 application. Therefore, the near-distance is the distance between the wave source $S_{aa}$ (or $S_{ab}$) and detector $D_{ba}$ (or $D_{bb}$), while the far-distance is to the diagonal length between the wave source $S_{aa}$ (or $S_{ab}$) and detector $D_{bb}$ (or $D_{ba}$). The same applies to the scanning unit, $T_b$, of FIG. 2G, except that the sensors are reversely arranged.

FIG. 2H is a schematic diagram of yet another trapezoidal scanning unit according to the present invention, where the scanning unit, $T_c$, is substantially similar to those of FIGS. 2F and 2G, except that the upper vertices of the trapezoid are separated by a greater distance than the lower vertices thereof. As discussed above, the distances between the adjacent sensors may also be adjusted as long as two opposing sides of the trapezoid have equal lengths and the foregoing sensitivity limitation is met by the wave detectors.

FIG. 3A is a schematic diagram of a quasi-linear scanning unit according to the present invention, where the scanning unit, $P_a$, includes two wave detectors, $D_{ba}$ and $D_{bb}$, disposed in the center portion thereof, where the first wave source, $S_{aa}$, is disposed at the upper-right corner of the scanning unit, and where the second wave source, $S_{ca}$, is disposed at the lower-left corner thereof. In particular, the wave sources, $S_{ca}$ and $S_{aa}$, are arranged at the same angle from the wave detectors, $D_{ba}$ and $D_{bb}$, respectively, and they are spaced apart therefrom by the same distance so that the wave sources and detectors are symmetrically arranged with respect to point of symmetry 128. Therefore, the foregoing embodiment also satisfies the symmetry requirements of the wave sources and detectors of the co-pending '972 application.

FIG. 3B is a schematic diagram of a rectangular scanning unit according to the present invention, where a first horizontal scanning element including the sensors, $S_{aa}$ and $D_{ab}$, is disposed over or above a second horizontal scanning element including sensors, $D_{ba}$ and $S_{ab}$, and where such sensors 122, 124 occupy four vertices of the rectangle. In this embodiment, the near-distance is the vertical distance between the wave source $S_{aa}$ (or wave detector $D_{ab}$) and wave detector $D_{ba}$ (or wave source $S_{bb}$), while the far-distance corresponds to the diagonal length between the wave sources (or detectors). It is also appreciated that sensors 122, 124 may be grouped to define a first vertical scanning element ($S_{aa}$ and $D_{ba}$) and a second vertical scanning element ($D_{ab}$ and $S_{bb}$). As will be described in greater detail below, the optical imaging system may be arranged to group sensors 122, 124 to define such scanning elements. FIG. 3C shows a schematic diagram of a parallelogram scanning unit according to the present invention. The scanning unit, $P_b$, includes a first pair of sensors, $S_{aa}$ and $D_{ab}$, which are disposed at two upper vertices of the parallelogram as well as a second pair of sensors, $D_{ba}$ and $S_{ab}$, which are disposed at two lower vertices thereof the rectangle.

The scanning units, $P_a$, $R_b$, and/or $P_b$, may have source-detector arrangements which are reverse to those shown in FIGS. 3A to 3C by, e.g., substituting the wave source by the wave detector and vice versa. In addition, as far as the foregoing sensitivity limitation is met by the wave detectors, distances between the wave sources and/or detectors may also be adjusted to manipulate the shape and/or size of the resulting scanning unit and its scanning area. Furthermore, the near- and far-distances in each scanning unit, $P_a$, $R_b$, and $P_b$, may be reversed by adjusting an aspect ratio of the source-detector arrangement, where the aspect ratio is defined as a ratio of a length to a height of a quadrangle. In the scanning unit, $P_b$, of FIG. 3C, e.g., the horizontal distance between the wave source, $S_{aa}$, and wave detector, $D_{ab}$, may be either a near-distance (e.g., when the aspect ratio is less than 1.0) or a far-distance (e.g., when the aspect ratio is greater than 1.0). When the aspect ratios of such scanning units approach 1.0, the distances between one wave source and two adjacent wave detectors become identical, and the symmetry requirement of the co-pending '972 application cannot be met. This may be contrasted with the source-detector arrangements in FIGS. 2C and 2D where the foregoing symmetry requirement is met by the square scanning units, $S_a$ and $S_b$.

Due to the irradiation and/or sensitivity limitations of the wave sources and detectors, each of the foregoing scanning units covers only a small scanning area. Thus, as shown in FIGS. 1A and 1B, optical probe 120 of the optical imaging system of the present invention typically includes multiple scanning units on the scanning surface thereof so that optical probe 120 can scan the target area which is generally larger than the scanning areas of individual scanning units thereof. Although such scanning units can be arranged in a symmetric or asymmetric manner and in any combination and/or permutation thereof, it is preferred that multiple scanning units be arranged to share one or more wave sources and/or detectors in order to increase efficiency of utilizing the finite scanning area and to enhance resolution of the resulting images. In other words, the optical probes or optical imaging system includes an imaging member that defines multiple scanning elements and multiple scanning units while incorporating some or all of the wave sources and/or detectors into more than one scanning element and/or scanning unit This aspect of the invention is now discussed using optical probe 120 of FIG. 1A as the exemplary embodiment.

Figure 4A:
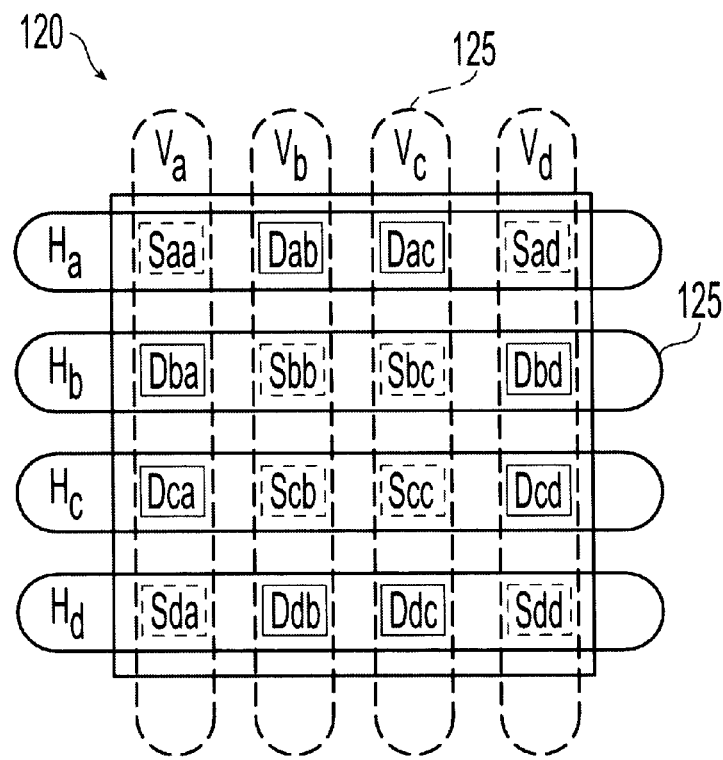
FIG. 4A is a schematic diagram of a first set of scanning units of the optical probe of FIG. 1A according to the present invention.
Figure 4B:
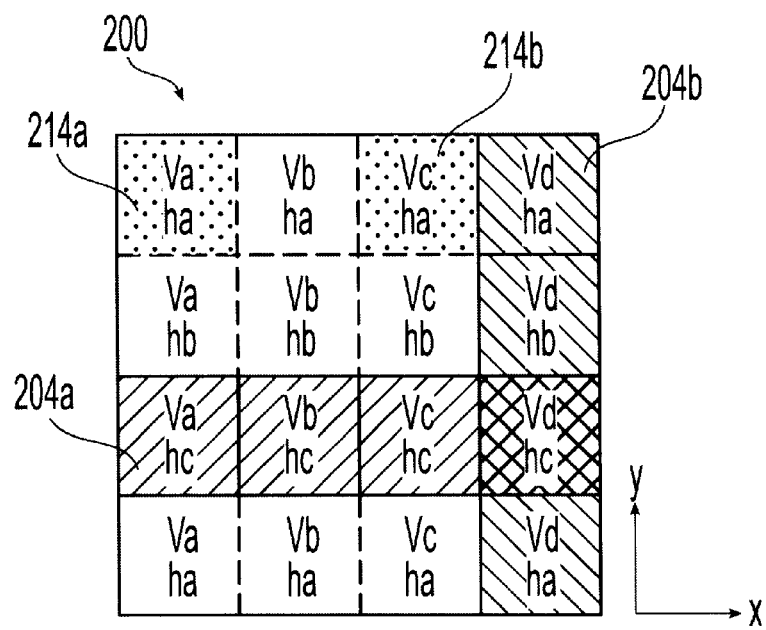
FIG. 4B is a schematic diagram of voxels and cross-voxels generated by the scanning units of FIG. 4A and resulting voxel values and cross-voxel values according to the present invention.

FIG. 4A is a schematic diagram of a first set of scanning units of the optical probe of FIG. 1A, and FIG. 4B is a schematic diagram of voxels and cross-voxels generated by the scanning units of FIG. 4A, and resulting voxel values and cross-voxel values thereof according to the present invention. Optical probe 120 includes four horizontal scanning units ($H_a$, $H_b$, $H_c$, and $H_d$) and four vertical scanning units ($V_a$, $V_b$, $V_c$, and $V_d$), where each scanning unit 125 generates one or more output signals which correspond to representative values of the chromophores or their properties in the target area of the medium scanned by each scanning unit 125.

As shown in FIG. 4B, each scanning unit 125 defines a "voxel" in an image domain 200, in which each voxel in image domain 200 corresponds to a small region of the target area of the medium in which one or more wave sources 122 irradiate electromagnetic waves into such a region and one or more wave detectors 124 detect such electromagnetic waves and generate output signals in response thereto. Thereafter, the imaging member of optical probe 120 or optical imaging system samples the output signal generated by wave detectors 124, solves a set of wave equations applied to wave sources 122 and detectors 124 of the same scanning unit 125, and determines a representative value of the chromophores or their properties therein. That is, the imaging member defines the scanning elements based on pre-determined groupings of wave sources 122 and detectors 124, spatially groups two or more overlapping or non-overlapping scanning elements so as to construct scanning units 125, samples the output signal generated by wave detectors 124 for each scanning unit, obtains the foregoing set of solutions from the wave equations, and calculates a voxel value per each voxel. Each voxel value is generally an area- or volume-averaged value of the chromophores or their properties which is generally averaged with respect to each scanning area or volume of scanning unit 125 or with respect to the area or volume of each voxel that is constructed in image domain 200. It is appreciated that the area-averaged voxel value is substantially similar or identical to the volume-averaged voxel value when wave detectors 124 have the sensitivity range covering a substantially identical thickness or depth of the medium throughout the entire target area.

In the embodiment shown in FIG. 4A, the horizontal scanning units, $H_a$, $H_b$, $H_c$, and $H_d$, define, in image domain 200, four parallel horizontal voxels 204a each of which is elongated in the X direction and stacked one over the other in a sequential mode. Based on the output signals generated by each of the horizontal scanning units, $H_a$, $H_b$, $H_c$, and $H_d$, the imaging member solves the wave equations applied to each horizontal scanning unit and determines the voxel value of $h_a$, $h_b$, $h_c$, and $h_d$ for each horizontal voxel 204a, respectively. For simplicity of presentation, FIG. 4B highlights only one horizontal voxel 204a (the third from the top) which has the voxel value of $h_c$. Similarly, the four vertical scanning units, $V_a$, $V_b$, $V_c$, and $V_d$, define four vertical voxels 204b which are elongated in the Y direction, sequentially and laterally arranged side by side, and have the voxel values of $v_a$, $v_b$, $v_c$, and $V_d$, respectively. For simplicity of illustration, FIG. 4B again highlights only one vertical voxel 204b having the voxel value of $v_d$.

As shown in the figure, each horizontal scanning unit shares one common optical sensor with one of the vertical scanning units, thereby defining cross-voxels as the overlapping regions of the intersecting horizontal and vertical voxels. Accordingly, optical probe 120 of FIG. 4A defines sixteen cross-voxels forming a 4×4 matrix in image domain 200, each having a separate cross-voxel value that is determined by two generally different voxel values of the intersecting voxels. For example, though two cross-voxels 214a, 214b are commonly defined in the top horizontal voxel, $H_a$, having the voxel value of $h_a$, the cross-voxel value of cross-voxel 214a is calculated from $v_a$ and $h_a$, whereas that of cross-voxel 214b is obtained from $v_c$ and $h_a$. In general, the cross-voxel values are calculated by, e.g., arithmetically averaging, geometrically averaging or weight-averaging individual voxel values of the intersecting voxels. In the alternative, one of such constituent voxel values may be selected as the cross-voxel value as well. It is noted that, other things being equal, accuracy of estimated values of the chromophores and/or their properties and resolution of the images of the distribution thereof generally depend on the size of the voxels, size of the cross-voxels, and the number of output signals or voxel values used to calculate the voxel values or cross-voxel values, respectively. In this aspect, each of the square cross-voxels of FIG. 4B has the substantially identical resolution across entire image domain 200.

The optical probes of the present invention with the foregoing embodiment offers numerous benefits. By arranging the scanning units to share one or more common optical sensors, the optical probe requires fewer number of the wave sources and detectors. Accordingly, the foregoing optical probes may be provided as compact and light articles. In addition, idiosyncratic discrepancies attributed to component variances inherent in each of the optical sensors may be minimized, thereby improving accuracy and enhancing quality and resolution of the resulting images. Furthermore, the optical probes of the present invention do not need baseline measurements, which is generally mandatory in prior art optical imaging systems. Therefore, the optical probes of the present invention efficiently construct images and provide real-time images of the distribution of the chromophores or their properties on a substantially real time basis during scanning of the target area of a test subject.

In operation, optical probe 120 is placed on a target area of the medium with each of its optical sensors forming appropriate optical coupling therewith. Wave sources 122 are activated to irradiate electromagnetic waves into the medium and wave detectors 124 are also turned on to detect the electromagnetic waves transmitted through the medium. In order to minimize interferences and noises therefrom, wave sources 124 are preferably synchronized such that only one wave source irradiates electromagnetic waves having pre-selected wave characteristics for a pre-selected period during which other wave sources are turned off. Wave detectors 124 are also synchronized such that only those wave detectors which form the scanning elements with the firing wave source detect electromagnetic waves and generate output signals in response thereto. After the selected wave source completes irradiation, the same or another wave source then commences irradiation of electromagnetic waves having identical or different wave characteristics. After all source-detector pairs of the first scanning unit of optical probe 120 complete the foregoing irradiation and detection of electromagnetic waves, similar or identical operations are repeated for the next scanning unit of optical probe 120. Sequence of such irradiation and/or detection generally does not affect operational characteristics of optical probe 120 and the final images representing the distribution of the chromophores or their properties. Selection of an optimum sequence is generally a matter of choice of one of ordinary skill in the art. The imaging member of the optical probe or optical imaging system samples and acquires such output signals at a pre-selected rate and/or duration for every scanning element of each scanning unit. The imaging member then processes the output signals and solves the set of wave equations applied to wave source 122 and detector 124 of each scanning element of the scanning unit of optical probe 120. The resulting solutions reflect absolute or relative values of the chromophores or their properties in each voxel in image domain 200. The imaging member then applies another grouping of such voxel values by, e.g., identifying intersecting and/or overlapping portions of two or more foregoing voxels, constructing cross-voxels corresponding to such intersecting or overlapping voxels, constructing residual voxels corresponding to residual portions of the voxels after carving out the cross-voxels therefrom, and obtaining cross-voxel values for each cross-voxels. The foregoing voxel values and cross-voxel values are reorganized such that the images of the distribution of the chromophores or their properties are represented by the voxel values and cross-voxel values. In the alternative, instead of calculating the voxel values and then averaging such to obtain the cross-voxel values for each of the cross-voxels, the output signals for the voxels can be averaged to yield the output signals for each cross-voxel, which are then processed by the imaging member to yield the cross-voxel value.

In general, configuration of voxels is determined by various factors such as the number of wave sources and detectors defining each scanning element and/or scanning unit, geometric arrangement of wave source and detectors in each scanning element and/or scanning unit, geometric arrangement of scanning elements in each scanning unit, emission power or irradiation capacity of wave sources, detection sensitivity of wave detectors, and the like. Thus, when the wave sources have same emission power and the wave detectors are provided with identical sensitivity, the equi-spaced source-detector arrangement of FIG. 4A defines the horizontal and vertical voxels having substantially identical configurations and the identical cross-voxels all across the image domain. The same also applies to the configuration of the cross-voxels which is predominantly determined by, e.g., configuration of voxels, disposition and orientation thereof, the shapes and sizes of their overlapping portions, and the like.

Although physical configuration of the foregoing voxels is rather fixed by the shapes, sizes, and operational characteristics of the wave sources and detectors and by the geometric arrangement thereof, configuration of the cross-voxels may be manipulated by grouping of the wave sources and detectors (i.e., defining the scanning elements and/or scanning unit) as well as by grouping of the scanning elements (i.e., defining the scanning units). In other words, without varying the physical arrangements of the wave sources and detectors, the shapes and sizes of the cross-voxels can be adjusted and the resolution of the resulting images can be manipulated by grouping output signals according to a pre-selected pattern and by solving the wave equations applied to the wave sources and detectors of such scanning elements and/or scanning units. Therefore, the optical probes may be arranged to define primary scanning units as well as secondary scanning units, and generate primary as well as secondary output signals from the same target area without implementing additional optical sensors to the optical probe and without physically altering the pre-existing source-detector arrangements thereof. FIGS. 5 through 7 show various scanning units additionally defined in exemplary optical probe 120 of FIG. 1A, and FIG. 8 shows the resulting voxels, cross-voxels, and cross-voxel values thereof obtained by combining the voxel values which are described in FIG. 4 through 7.

FIG. 5A shows a schematic diagram of a second set of scanning units of the optical probe of FIG. 1A according to the present invention. FIG. 5B represents voxels and cross-voxels generated by such scanning units, while FIG. 5C shows resulting voxel values and cross-voxel values thereof according to the present invention. In this embodiment, the optical sensors arranged in intermediate regions of the optical probe are regrouped to form four rectangular or square scanning units, $I_a$, $I_b$, $I_c$, and $I_d$. Similar to those shown in FIGS. 2C to 2E, the optical sensors of each of these intermediate scanning units, $I_a$, $I_b$, $I_c$, and $I_d$, satisfy the foregoing symmetry requirements of the '972 application. Thus, rectangular or square voxels 205a–205d are defined in image domain 200, each having a voxel value of $i_a$, $i_b$, $i_c$, and $i_d$, respectively. Because the foregoing intermediate voxels 205a–205d intersect each other in the center portion of image domain 200, the imaging member can also define multiple rectangular or square cross-voxels 215a while leaving residual truncated voxels 215b therein. For example, each cross-voxel 215a is of one quarter size of the rectangular or square voxel 205a–205d, while the residual truncated voxels 215b have one half the size thereof. In addition, similar to the embodiment shown in FIGS. 4A and 4B, the cross-voxel values of rectangular or square cross-voxels 215a are determined by two voxel values, i.e., their original voxel value and that of a neighboring voxel. Accordingly, optical probe 120 of FIG. 5A can provide images with higher resolution in the center portion of image domain 200. It is appreciated that the four corners 215c of image domain 200 carry neither voxel value nor the cross-voxel value, because none of the scanning units 204d–205d cover such regions.

FIG. 6A is a schematic diagram of a third set of scanning units of the optical probe of FIG. 1A according to the present invention. FIG. 6B is a schematic diagram of voxels and cross-voxels generated by the scanning units of FIG. 6A, while FIG. 6C shows another schematic diagram of resulting values for the voxels and cross-voxels of FIG. 6B according to the present invention. In this embodiment, optical probe 120 (or its imaging member) synchronizes the wave sources and detectors and defines four diamond-shaped scanning units, $C_a$, $C_b$, $C_c$, and $C_d$, therein. It is noted that these diamond-shaped scanning units correspond to the rectangular or square scanning units of FIGS. 2C to 2E which are tilted by 45°. Although each diamond-shaped scanning unit only includes optical sensors disposed at four corners of the diamond region and does not include any wave source or detector in its middle portion, the region of the target area of the medium corresponding to such middle portion in image domain 200 is nevertheless irradiated by wave sources 122 and scanned by each scanning element of each diamond-shaped scanning unit. Therefore, the diamond-shaped scanning units, $C_a$, $C_b$, $C_c$, and $C_d$, define a cross-shaped voxels 206a-206d each of which has four prongs connected to a center region and each of which carries voxel value of $c_a$, $c_b$, $c_c$, and $c_d$, respectively. Each of the diamond-shaped scanning units further intersects two adjacent scanning units, thereby forming cross-voxels 216a while leaving out residual, non-intersecting prongs of original voxels 216b as depicted in FIGS. 6B and 6C. It is appreciated that, contrary to those of FIGS. 4 and 5, the cross-voxel values of all cross-voxels 216a of this embodiment are determined by the voxel values of three intersecting cross-shaped voxels, i.e., its own voxel value plus two other voxel values of adjacent cross-shaped voxels. As a result, cross-voxels 216a of FIG. 6C can provide the images with resolution higher than that of FIGS. 4C and 5C. Furthermore, similar to the rectangular or square scanning units, $I_a$, $I_b$, $I_c$, and $I_d$, of FIG. 5A, diamond-shaped scanning units, $C_a$, $C_b$, $C_c$, and $C_d$, do not scan four corners 216c of image domain 200 and, therefore, provide neither voxel values nor cross-voxel values for such regions. In this context, the diamond-shaped scanning units, $C_a$, $C_b$, $C_c$, and $C_d$, define cross-voxels 216a which are identical to those defined by intermediate scanning units, $I_a$, $I_b$, $I_c$, and $I_d$, but whose cross-voxel values are determined by three voxel values instead of two.

Figure 7A:
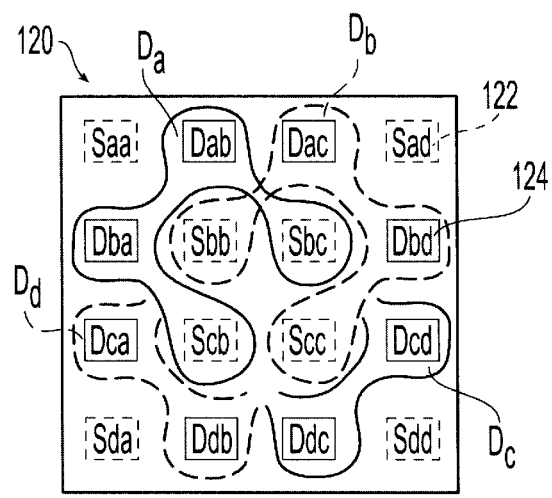
FIG. 7A is a schematic diagram of a fourth set of scanning units of the optical probe of FIG. 1A according to the present invention.
Figures 7B, 7C:
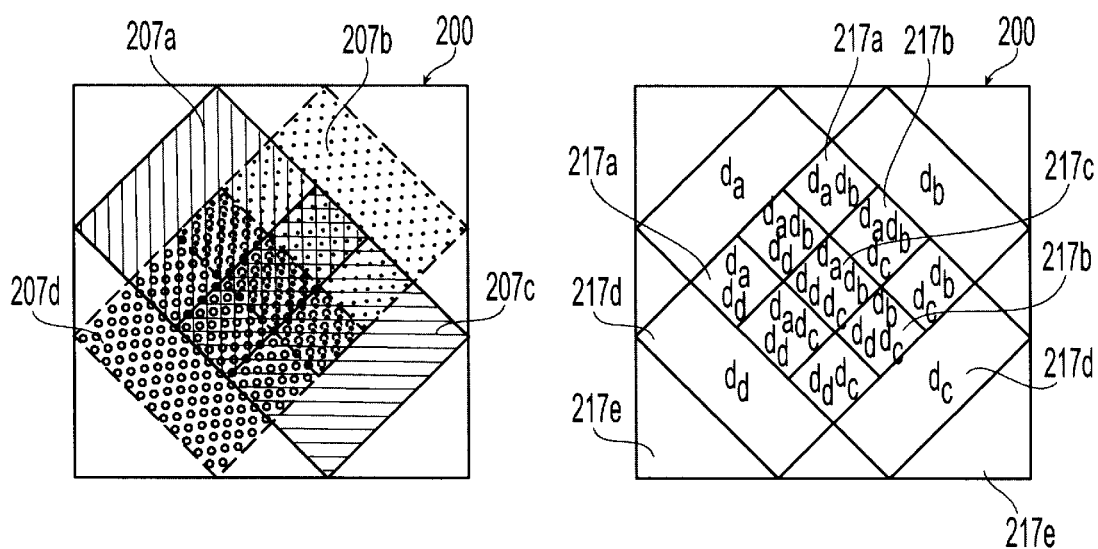
FIG. 7B is a schematic diagram of voxels and cross-voxels generated by the scanning units of FIG. 7A according to the present invention.
FIG. 7C is a schematic diagram of voxel values and cross-voxel values of FIG. 7B according to the present invention.
Figure 8:
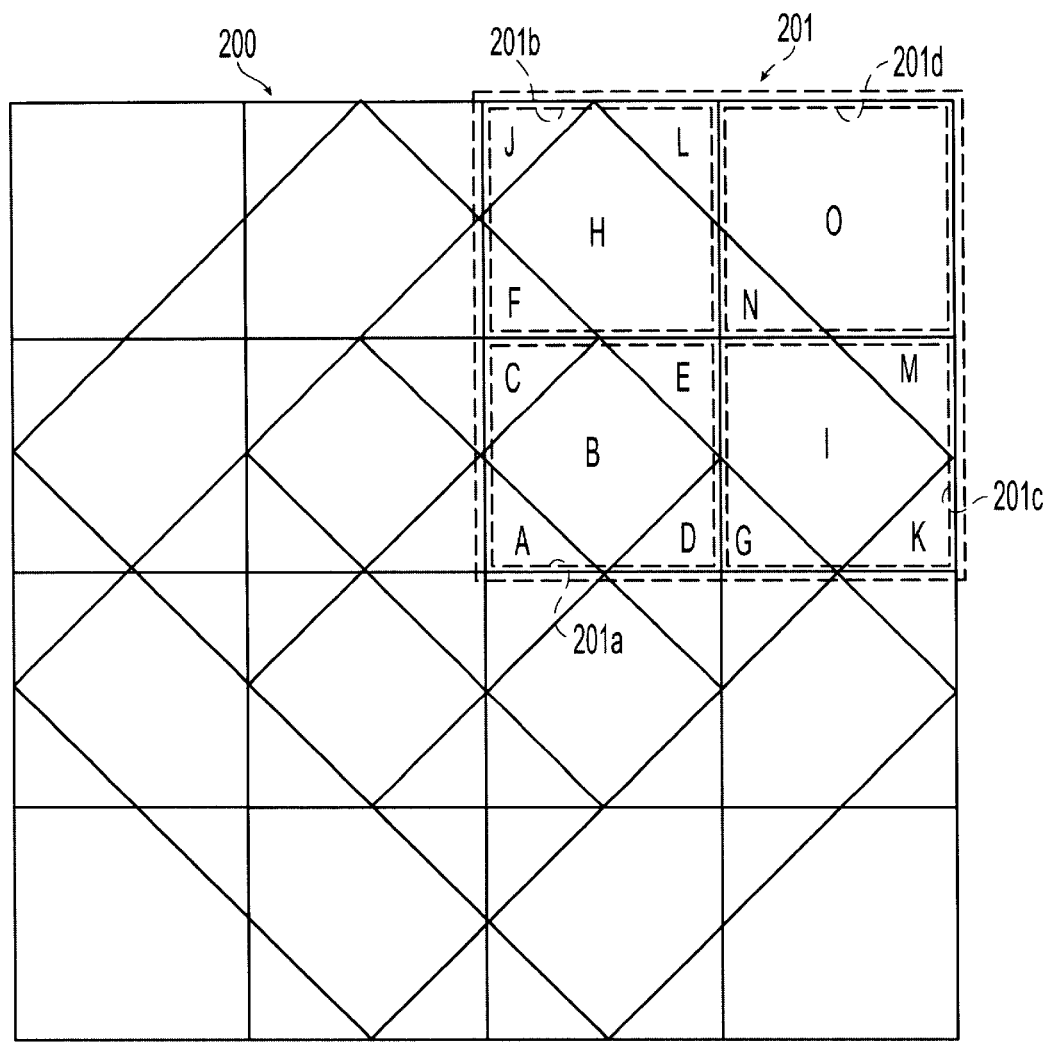
FIG. 8 is a schematic diagram of the voxels of FIGS. 4 through 7 and cross-voxels therefrom according to the present invention.

FIG. 7A is a schematic diagram of a fourth set of the scanning units of the optical probe of FIG. 1A according to the present invention. FIG. 7B represents a schematic diagram of voxels and cross-voxels generated by the scanning units of FIG. 7A, while FIG. 7C is yet another schematic diagram of resulting values and cross-voxel values of FIG. 7B according to the present invention. In this embodiment, the wave sources and detectors are regrouped to define four other diamond-shaped scanning units, $D_a$, $D_b$, $D_c$, and $D_d$, which are identical to those, $C_a$, $C_b$, $C_c$, and $C_d$, of FIG. 6A. However, the imaging member of optical probe 120 or optical imaging system is arranged to define diamond-shaped voxels 207a–207d, each of which intersects all three other scanning units. Therefore, diamond-shaped scanning units, $D_a$, $D_b$, $D_c$, and $D_d$, define nine smaller diamond-shaped cross-voxels 217a–217c in the center portion of imaging domain 200 while leaving four truncated voxels 216d around corners of imaging domain 200 as shown in FIGS. 7B and 7C. In general, all cross-voxels 217a–217c have identical shapes and sizes. It is appreciated, however, that the cross-voxel value of center cross-voxel 217c is calculated from the voxel values of all four diamond-shaped voxels 207a–207d, while the cross-voxel values of corner cross-voxels 217a and middle cross-voxels 217b are determined by two and three voxel values of the adjacent voxels, respectively. Thus, optical probe 120 of FIG. 7A can provide the images with its resolution increasing concentrically from the outer to the center portion thereof. Similar to the scanning units of FIGS. 5A and 6A, the diamond-shaped scanning units, $D_a$, $D_b$, $D_c$, and $D_d$, do not scan four triangular corners 217e of image domain 200 either.

As discussed above, the number of wave sources and detectors included in each scanning unit and geometric arrangement thereof are not necessarily dispositive of the shapes and sizes of the voxels and cross-voxels as well as of the resolution of the resulting images. Rather, accuracy of estimated values of the chromophore properties and resolution of the images thereof can be improved by manipulating the grouping pattern of the output signals. For example, the imaging member of the optical probe or optical imaging system of the present invention may combine one or more of the foregoing secondary scanning units of FIGS. 5 through 7 with the primary scanning units of FIG. 4A. This embodiment is generally preferred when it is desirable to obtain images with higher resolution as will be discussed in greater detail below. FIG. 8 is a schematic diagram of the resulting voxels and cross-voxels obtained by implementing the secondary scanning units of FIGS. 5 through 7 into those of FIG. 4 according to the present invention. As shown in FIG. 7, each quadrant of image domain 200 includes fifteen cross-voxels and/or residual voxels. Because all of the foregoing voxels and cross-voxels are constructed symmetric with respect to a center of image domain 200, only those images on the first quadrant 201 of image domain 200 is analyzed as a representative example of the images on entire image domain 200. Only for illustration purposes, first quadrant 201 is further divided into four sub-quadrants 201a–201d, where a first sub-quadrant 201a has five cross-voxels (A through E), a second sub-quadrant 201b includes four cross-voxels (F, J, H, and L), a third sub-quadrant 201c has another four cross-voxels (G, I, K, and M), and a fourth sub-quadrant 201d includes one cross-voxel (N) as well as one truncated background voxel (O).

Because all four sub-quadrants 201a–201d have the identical area in imaging domain 200, the resolution of the images in each sub-quadrant 201a–201d is expected to be proportional to the number of the cross-voxels provided therein as well as the number of voxel values used to determine the cross-voxel values thereof. Therefore, the sub-quadrant 201a has the highest resolution, while the sub-quadrant 201d has the lowest. This result is tabulated in Table 1 which enumerates every voxel value which are to be used to calculate each cross-voxel of the first quadrant 201.

TABLE 1

| Cross-Voxel | Voxel Values | No. |
| --- | --- | --- |
| A | $v_c, h_b, i_a, i_b, c_a, c_b, c_c, d_a, d_b, d_c, d_d$ | 11 |
| B | $v_c, h_b, i_a, i_b, c_a, c_b, c_c, d_a, d_b, d_c$ | 10 |
| C | $v_c, h_b, i_a, i_b, c_a, c_b, c_c, d_a, d_b$ | 9 |
| D | $v_c, h_b, i_a, i_b, c_a, c_b, c_c, d_b, d_c$ | 9 |
| E | $v_c, h_b, i_a, i_b, c_a, c_b, c_c, d_b$ | 8 |
| F | $v_c, h_a, i_a, c_b, d_a, d_b$ | 6 |
| G | $v_d, h_b, i_b, c_b, d_b, d_c$ | 6 |
| H | $v_c, h_a, i_a, c_b, d_b$ | 5 |
| I | $v_d, h_b, i_b, c_b, d_b$ | 5 |
| J | $v_c, h_a, i_a, c_b,$ | 4 |
| K | $v_d, h_b, i_b, c_b,$ | 4 |
| L | $v_c, h_a, i_a, c_b,$ | 4 |
| M | $v_d, h_b, i_b, c_b,$ | 4 |
| N | $v_d, h_b, d_b$ | 3 |
| O | $v_d, h_a$ | 2 |

As listed in Table 1, the value of each cross-voxel is determined by multiple voxel values ranging from two voxels (for the pentagonal, corner cross-voxel "O"), three voxels (for the adjacent triangular cross-voxel "N"), and up to ten voxels (for the center diamond-shaped cross-voxel "B") and eleven voxels (for the center triangular cross-voxel "A"). The results indicate that, without changing physical configuration of optical probes 120, the accuracy of the estimated chromophore properties as well as the resolution of the images may be adjusted solely by manipulating the grouping pattern of the wave sources and detectors and that of the output signals generated by such wave detectors.

Similarly, the accuracy of the estimated chromophore properties as well as the resolution of the resulting images may readily be adjusted by controlling the number of secondary scanning units to be incorporated into the primary scanning unit. For example, only a pre-selected set(s) of secondary scanning units may be combined with the primary scanning units of FIG. 4. Such selections may be encoded so that an operator may choose one of the pre-determined combinations which yield various image resolution and/or which may adjust image resolutions around a specific region of the target area. It is appreciated that, without the voxel values ($d_a$, $d_b$, $d_c$, and $d_d$) of the diamond-shaped voxels of FIGS. 7B and 7C, all cross-voxels A through E in the first sub-quadrant 201a are estimated by the identical number of voxel values (i.e., seven voxels thereof), thereby yielding the identical resolution thereacross.

The foregoing scanning elements and scanning units of the optical probe or optical imaging system of the present invention may be modified to provide optical probes which have different source-detector arrangements and/or configurations without departing from the scope of the present invention.

As briefly discussed above, a single wave source may include two or more wave generators so that the wave source including multiple wave generators (referred to as "composite wave source" hereinafter) irradiate electromagnetic waves having two different wave characteristics, e.g., two different wavelengths. Such composite wave sources can be applied to any of the foregoing source-detector arrangements. For example, in FIG. 2B, the wave sources, $S_{ab}$ and $S_{ac}$, of the scanning unit, Hf, can be arranged to irradiate near-infrared electromagnetic waves with the wavelengths of about 690 m and 830 nm, thereby allowing a single scanning unit to generate at least two output signals that represent different optical interaction of the chromophores with such different electromagnetic waves.

Figure 9A:
FIG. 9A is a schematic diagram of an asymmetric scanning unit satisfying the symmetry requirement according to the present invention.
Figure 9B:
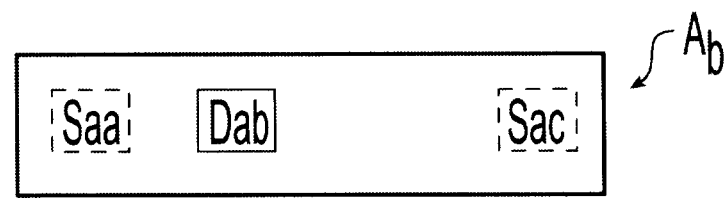
FIG. 9B is a schematic diagram of another asymmetric scanning unit which satisfies the symmetry requirement according to the present invention.
Figure 9C:
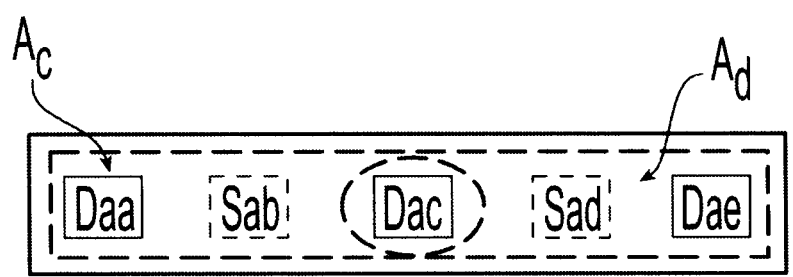
FIG. 9C is a schematic diagram of yet another asymmetric scanning unit that satisfies the symmetry requirement according to the present invention.

Such composite wave sources can also be employed to provide asymmetric scanning units which can still satisfy the symmetry requirements of the co-pending '972 application. FIGS. 9A to 9C are a few exemplary embodiments of such scanning units.

FIG. 9A is a schematic diagram of an asymmetric scanning unit satisfying the symmetry requirements of the co-pending '972 application according to the present invention. An exemplary asymmetric scanning unit, $A_a$, includes two wave detectors, $D_{aa}$ and $D_{ac}$, and a composite wave source, $S_{ab}$, interposed therebetween. The wave detectors, $D_{aa}$ and $D_{ac}$, are disposed at both ends of scanning unit, $A_a$, while the wave source, $S_{ab}$, is disposed in a middle but off-center portion of the scanning unit, $A_a$, such that the distance between the wave detector, $D_{aa}$, and the composite wave source, $S_{ab}$, corresponds to a first near-distance between a first wave generator and the wave detector, $D_{aa}$, as well as a second near-distance between a second wave generator and the wave detector, $D_{aa}$. Similarly, the distance between the wave detector, $D_{ac}$, and the composite wave source, $S_{ab}$, corresponds to a first far-distance between a first wave generator and the wave detector, $D_{ac}$, as well as a second far-distance between a second wave generator and the wave detector, $D_{ac}$. Thus, the asymmetric scanning unit, $A_a$, satisfies the symmetry requirements of the '972 application. FIG. 9B is a schematic diagram of another asymmetric scanning unit which satisfies the symmetry requirements according to the present invention, where a second asymmetric scanning unit, $A_b$, includes two wave sources, $S_{aa}$ and $S_{ac}$, and a composite wave detector, $D_{ab}$, interposed therebetween. Similar to the embodiment of FIG. 9A, the wave detector, $D_{ab}$, detects the electromagnetic waves emitted from two wave sources, $S_{aa}$ and $S_{ac}$, while satisfying the symmetry requirements.

It is noted that the foregoing three-sensor arrangements shown in FIGS. 9A and 9B may not be as efficient as the four-sensor arrangements disclosed hereinabove. For example, the scanning units of the three-sensor arrangement scans the target area without overlapping any regions thereof. Therefore, such single-coverage may generally result in less accurate estimated values of the chromophore properties as well as final images with lower resolution. However, by grouping the wave sources and detectors to form the three- and/or four-sensor source-detector arrangements, such disadvantages are readily obviated. FIG. 9C is a schematic diagram of scanning units defined by various three- and/or four-sensor source-detector arrangements according to the present invention. An optical probe 120 includes two wave sources, $S_{ab}$ and $S_{ad}$, and three wave detectors, $D_{aa}$, $D_{ac}$, and $D_{ac}$, and defines two asymmetric scanning units, $A_c$, and $A_d$, where two three-sensor scanning units share one common wave detector, $D_{ac}$. It is appreciated that the wave sources, $S_{ab}$ and $S_{ad}$, and wave detectors, $D_{aa}$ and $D_{ac}$, may also be grouped to define a symmetric scanning unit as well. As discussed above, the optical probe and optical imaging system of the invention are versatile to define primary and secondary scanning units each of which may be symmetric or asymmetric.

Figure 10A:
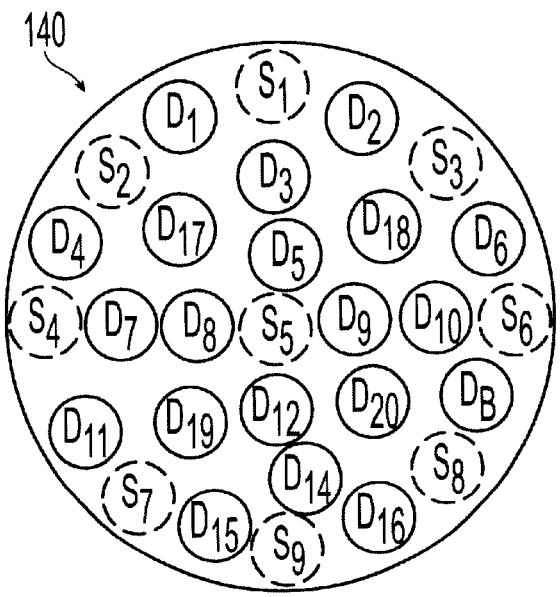
FIG. 10A is a schematic diagram of an exemplary circular optical probe of an optical imaging system according to the present invention.
Figure 10B:
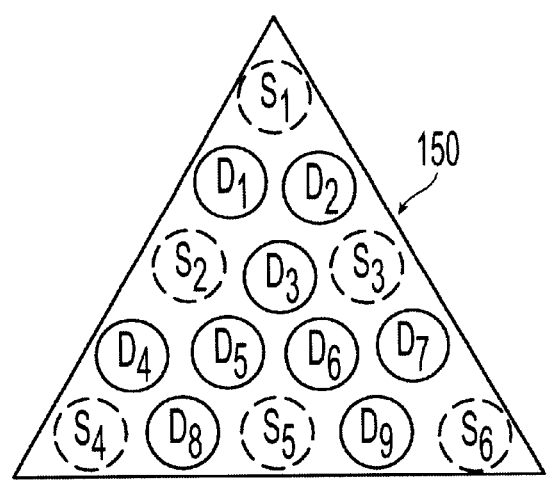
FIG. 10B is a schematic diagram of an exemplary triangular optical probe of an optical imaging system according to the present invention.

The foregoing scanning units described in FIGS. 2A to 2H, FIGS. 3A to 3C, and FIGS. 9A to 9C may also be arranged to yield optical probes having various shapes and sizes. FIG. 10A is a schematic diagram of an exemplary circular optical probe of an optical imaging system according to the present invention where the wave sources and detectors are disposed on a circular scanning surface, whereas FIG. 10B is another schematic diagram of an exemplary triangular optical probe of an optical imaging system according to the present invention where the sensors are disposed on a triangular scanning surface.

A circular optical probe 140 of FIG. 10A includes nine wave sources ($S_1$ to $S_9$) and twenty wave detectors ($D_1$ to $D_{16}$) on its circular scanning surface. Depending on requisite resolution, an imaging member may group these sensors and define a variety of scanning units therefrom. For example, the imaging member may define linear scanning units (e.g., $S_1$-$D_3$-$D_5$-$S_5$, $S_5$-$D_9$-$D_{10}$-$S_6$, $S_1$-$D_3$-$D_{14}$-$S_9$, $S_1$-$D_5$-$D_{12}$-$S_9$, $S_3$-$D_{18}$-$D_{19}$-$S_7$, and the like), rectangular and/or trapezoidal scanning Units (e.g., $S_2$-$D_3$-$S_5$-$D_7$, $S_2$-$S_3$-$D_{10}$-$D_7$, $S_1$-$D_1$-$D_1$-$S_1$, $S_1$-$D_2$-$D_6$-$S_8$, $S_1$-$D_2$-$D_{13}$-$S_8$, $S_1$-$D_{18}$-$D_{20}$-$S_9$, $S_1$-$D_6$-$D_{13}$-$S_9$, and the like), and so on. In addition, asymmetric scanning units may further be defined across the scanning surface as well. Similarly, an exemplary triangular optical probe 150 includes six wave sources ($S_1$ to $S_6$) and nine wave detectors ($D_1$ to $D_9$) which may be grouped to form linear, quasi-linear, rectangular, square, trapezoidal or parallelogram scanning units in addition to asymmetric scanning unit. By combining primary scanning units with secondary scanning units and by processing the output signals generated by the wave detectors of such scanning units, the imaging member of the optical probe or optical imaging system can provide the images of two- and/or three distribution of the chromophores and/or their properties meeting requisite image resolution. It is manifest from FIGS. 10A and 10B that additional wave sources and detectors are disposed inside the scanning units for which such additional wave sources do not irradiate electromagnetic waves and for which such wave detectors do not generate any output signals.

Although the foregoing disclosure of the invention is mainly directed to the images of spatial distribution of the chromophore properties, the optical probes and optical imaging system of the present invention may also be applied to generate images of temporal distribution thereof. For example, the optical probe may be arranged to scan a substantially same target area of the medium over a certain time interval. By obtaining the differences in the output signals detected at different time intervals in the same target area, the imaging member calculates temporal changes in the chromophore properties in the target area and generates the images of the temporal distribution of such properties. In the alternative, the temporal changes in the chromophore properties may be determined and their images may be provided from spatial distributions of such chromophore properties obtained in different time frames. For example, the scanning units of the optical probe may repeat scanning of the target area and calculate the temporal distribution pattern of the chromophore property. It is noted that the temporal changes and their distribution usually relate to relative changes in the chromophore properties. However, once the absolute values of such chromophore properties are determined in any reference time frame, preceding or subsequent changes in such properties can be readily converted to the absolute values thereof and vice versa.

It is noted that the foregoing optical probes and optical imaging systems of the present invention may also be arranged to provide values for the temporal changes in blood or water volume in the target area of the medium. In an exemplary embodiment for calculating such temporal changes in blood volume in a target area of a human subject, the concentration of oxygenated hemoglobin, [HbO], and that of deoxygenated hemoglobin, [Hb], are calculated by a set of equations (1a) and (1b) or by another set of equations (2a) and (2b). Once [Hb] and [HbO] are obtained, the sum (i.e., total hemoglobin concentration, [HbT], which is the sum of [Hb] and [HbO]) is obtained. By obtaining the output signals from the wave detectors positioned in the same target area over time, changes in the total hemoglobin concentration can be obtained. By assuming that hematocrit of blood (i.e., the volume percentage of the red blood cells in blood) flowing in and out of the target area is maintained at a constant level over time, temporal changes in the blood volume in the target area are directly calculated in terms of temporal changes in [HbT] in the target area. In the alternative, temporal changes in [Hb] and [HbO] may be calculated from the equations (6a) and (6b) and temporal changes in [HbT] is then obtained as the sum of changes in [Hb] and [HbO] in the target area.

It is also appreciated that the optical probes and optical imaging systems of the present invention may be applied to obtain the images of three-dimensional distribution of the chromophore properties in the target area of the medium. As discussed above, the electromagnetic waves are irradiated by the wave sources and transmitted through a target volume of the medium which is defined by a target area and a pre-determined thickness (or depth) into the medium. Accordingly, a set of wave equations can be formulated for such three-dimensional target volume, and the output signals generated by the wave detectors are provided to the imaging member which then solves the wave equations with relevant initial and/or boundary conditions, where such solutions from the wave equations represent the three-dimensional distribution of the chromophore properties in the target volume of the medium. To maintain the pre-selected resolution of the images, the optical imaging probes and/or systems preferably include a large number of wave sources and detectors defining a larger number of voxels in the target volume of the medium. Suppose that an exemplary optical probe or optical imaging system includes two wave sources and four wave detectors and generates two-dimensional images of a target area at a pre-selected resolution. When a target volume is defined to have the same target area and a pre-selected thickness including N two-dimensional layers stacked one over the other, such an optical imaging system may probably be required to include about 2N wave sources and 4N wave detectors in order to maintain the same resolution for each two-dimensional layer. The number of such wave sources and detectors may be reduced, however, by generating enough secondary scanning units over the target area, preferably overlapping each other. Thus, the optical probes or optical imaging systems require fewer number of wave sources and detectors by arranging the imaging member to define and incorporate enough number of secondary scanning units. It is noted, however, that resolution of images from any optical imaging system is inherently limited by the average "free walk distance" of photons in the physiological medium that is typically about 1 mm. In addition, due to sensitivity limitation or electronic and mechanical noise inherent in almost any optical imaging system, the best-attainable resolution of the images may be in the range of a few millimeters or about 1 mm to 5 mm for now. Thus, the foregoing voxels and cross-voxels which have dimensions less than 1 mm to 5 mm or, more particularly, about 1 mm may not necessarily enhance resolution of the final images.

The foregoing optical imaging systems and optical probes of the invention can also be used to determine intensive properties of the chromophores, e.g., concentration, sum of concentrations, and/or ratios of such concentrations. The foregoing optical imaging systems and optical probes may also be used to estimate extensive chromophore properties such as volume, mass, weight, volumetric flow rate, and mass flow rate thereof.

It is appreciated that the foregoing optical imaging systems, optical probes thereof, and methods therefor may be readily adjusted to provide images of distribution of different chromophores or properties thereof. Because different chromophores generally respond to electromagnetic waves having different wavelengths, the wave sources of such optical imaging systems and probes may be manipulated to irradiate electromagnetic waves interacting with pre-selected chromophores. For example, the near-infrared waves having wavelengths between 600 nm and 1,000 nm, e.g., about 690 nm and 830 nm are suitable to measure the distribution pattern of the hemoglobins and their property. However, the near-infrared waves having wavelengths between 800 nm and 1,000 um, e.g., about 900 nm, can also be used to measure the distribution pattern of water in the medium. Selection of an optimal wavelength for detecting a particular chromophore generally depends on optical absorption and/or scattering properties of the chromophore, operational characteristics of the wave sources and/or detectors, and the like.

The foregoing optical imaging systems, optical probes, and methods of the present invention may be clinically applied to detect tumors or stroke conditions in human breasts, brains, and any other areas of the human body where the foregoing optical imaging methods such as diffuse optical tomography is applicable. The foregoing optical imaging systems and methods may also be applied to assess blood flow into and out of transplanted organs or extremities and/or autografted or allografted body parts or tissues. The foregoing optical imaging systems and methods may be arranged to substitute, e.g., ultrasonogram, X-rays, EEG, and laser-acoustic diagnostic. Furthermore, such optical imaging systems and methods may be modified to be applicable to various physiological media with complicated photon diffusion phenomena and/or with non-flat external surface.

It is noted that the optical imaging systems, optical probes, and methods of the present invention may incorporate or be applied to related inventions and embodiments disclosed in the commonly assigned co-pending U.S. applications bearing Ser. No. 09/778,613 and entitled "Optical Imaging System for Direct Image Construction," bearing Ser. No. 09/778,618 and entitled "Self-Calibrating Optical Imaging System," and bearing Ser. No. 09/778,617 and entitled "Optical Imaging System with Direct Image Construction," all of which have been filed on Feb. 6, 2001 and all of which are incorporated herein in their entirety by reference.

It is to be understood that, while various embodiments of the invention has been described in conjunction with the detailed description thereof, the foregoing is only intended to illustrate and not to limit the scope of the invention, which is defined by the scope of the appended claims. Other embodiments, aspects, advantages, and modifications are within the scope of the following claims.

What is claimed is:

1. An optical probe for an optical imaging system capable of generating images representing distribution of hemoglobins or their properties in target areas of a physiological medium, said optical probe including a plurality of wave sources and wave detectors, said wave sources configured to form optical coupling with said medium and to irradiate near-infrared electromagnetic waves thereinto and said wave detectors configured to detect said near-infrared electromagnetic waves and configured to generate output signals in response thereto, said optical probe comprising:

a plurality of symmetrically disposed scanning units each of which including a first wave source, a second wave source, a first wave detector, and a second wave detector, said first wave source disposed closer to said first wave detector than said second wave detector and said second wave source disposed closer to said second wave detector than said first wave detector, wherein a first near-distance between said first wave source and said first wave detector is substantially similar to a second near-distance between said second wave source and said second wave detector, wherein a first far-distance between said first wave source and said second wave detector is substantially similar to a second far-distance between said second wave source and said first wave detector, and wherein said first and second wave detectors are configured to generate said output signals in response to said near-infrared electromagnetic waves irradiated by at least one of said first and second wave sources and detected thereby, said output signals representing optical interaction of said near-infrared electromagnetic waves with said hemoglobins in said target areas of said medium.

2. The optical probe of claim 1 wherein said first and second near-distances are at least substantially identical.

3. The optical probe of claim 1 wherein said first and second far-distances are at least substantially identical.

4. The optical probe of claim 1 wherein at least one of said symmetric scanning units includes an axis of symmetry with respect to which said first and second wave sources are symmetrically disposed and with respect to which said first and second wave detectors are symmetrically disposed.

5. The optical probe of claim 4 wherein at least two of said symmetric scanning units include at least one of a common wave source and a common wave detector.

6. The optical probe of claim 4 wherein said first and second wave sources and said first and second wave detectors are substantially linearly disposed.

7. The optical probe of claim 6 wherein said first and second wave sources are interposed between said first and second wave detectors.

8. The optical probe of claim 6 wherein said first and second wave detectors are interposed between said first and second wave sources.

9. The optical probe of claim 6 wherein said near-distance is about one half of said far-distance.

10. The optical probe of claim 6 wherein said optical probe includes at least one first symmetric scanning unit and at least one second symmetric scanning unit, wherein said first and second scanning units share said axis of symmetry, wherein said first scanning unit has a first arrangement of said wave sources and wave detectors, and wherein said second scanning unit has said first arrangement of said wave sources and detectors and is disposed below said first scanning unit.

11. The optical probe of claim 10 wherein said second scanning unit is disposed immediately below said first scanning unit.

12. The optical probe of claim 6 wherein said optical probe includes at least one first symmetric scanning unit and at least one second symmetric scanning unit, wherein said first and second scanning units share said axis of symmetry, wherein said first scanning unit has a first arrangement of said wave sources and wave detectors, and wherein said second scanning unit is disposed below said first scanning unit and has a second arrangement of said wave sources and wave detectors that is substantially reverse to said first arrangement.

13. The optical probe of claim 12 wherein said second scanning unit is disposed immediately below said first scanning unit.

14. The optical probe of claim 6 wherein said optical probe includes at least one first, second, third, and fourth symmetric scanning units each sharing said axis of symmetry with the others, wherein said first scanning unit has a first arrangement of said wave sources and wave detectors, wherein said second scanning unit is disposed immediately below said first scanning unit and has a second arrangement of said wave sources and wave detectors which is substantially reverse to said first arrangement, wherein said third scanning unit is disposed immediately below said second scanning unit and has said second arrangement, and wherein said fourth scanning unit is disposed immediately below said third scanning unit and has said first arrangement.

15. The optical probe of claim 14 wherein all of said symmetric scanning units have identical shapes and sizes and define a 4×4 source-detector arrangement wherein said wave sources and detectors of said symmetric scanning units are spaced at a uniform distance.

16. The optical probe of claim 15 wherein said 4×4 source-detector arrangement has a shape of a quadrangle which is one of a rectangle, a square, a parallelogram, and a diamond.

17. The optical probe of claim 4 wherein said first and second wave sources and said first and second wave detectors are arranged to form four vertices of a quadrangle, said first and second wave sources disposed at two upper vertices of said quadrangle, and said first and second wave detectors disposed at two lower vertices thereof.

18. The optical probe of claim 17 wherein said quadrangle is one of a trapezoid, rectangle, and square, said trapezoid having two opposing sides of equal lengths.

19. The optical probe of claim 17 wherein said optical probe includes at least one first symmetric scanning unit and at least one second symmetric scanning units, said first and second scanning units having different axes of symmetry, said first scanning unit having a first arrangement of said wave sources and detectors, and said second scanning unit disposed lateral to said first scanning unit and having said first arrangement.

20. The optical probe of claim 17 wherein said optical probe includes at least one first symmetric scanning unit and at least one second symmetric scanning units, said first and second scanning units having different axes of symmetry, said first scanning unit having a first arrangement of said wave sources and detectors, and said second scanning unit disposed lateral to said first scanning unit and having a second arrangement of said wave sources and detectors which is substantially reverse to said first arrangement.

21. The optical probe of claim 17 wherein said optical probe includes at least one first, second, third, and fourth symmetric scanning units, wherein said first scanning unit has a first arrangement of said wave sources and detectors, wherein said second scanning unit is disposed lateral to said first scanning unit and has a second arrangement of said wave sources and detectors which is substantially reverse to said first arrangement, wherein said third scanning unit is disposed immediately below said first scanning unit and has said second arrangement, and wherein said fourth scanning unit is disposed immediately below said second scanning unit and has said first arrangement.

22. The optical probe of claim 4 wherein a first set of said wave sources and detectors is substantially linearly disposed and wherein a second set of said wave sources and detectors is disposed to form four vertices of a quadrangle.

23. The optical probe of claim 22 wherein said first and second sets include at least one of a common wave source and a common wave detector.

24. The optical probe of claim 1 wherein at least one of said symmetric scanning units includes a point of symmetry with respect to which said first and second wave sources are symmetrically disposed and with respect to which said first and second wave detector are symmetrically disposed.

25. The optical probe of claim 24 wherein at least two of said symmetric scanning units include at least one of a common wave source and a common wave detector.

26. The optical probe of claim 24 wherein said first and second wave sources and said first and second wave detectors are substantially linearly disposed.

27. The optical probe of claim 24 wherein said first and second wave sources and said first and second wave detectors are disposed to form four vertices of a quadrangle, wherein said first wave source and detector are disposed at two upper vertices of said quadrangle, and wherein said second wave detector and source are disposed at two lower vertices thereof.

28. The optical probe of claim 27 wherein said quadrangle is one of a rectangle and a parallelogram, said parallelogram having two sides of different lengths.

29. The optical probe of claim 1 wherein at least one of said symmetric scanning units includes at least one of a third wave source and a third wave detector.

30. The optical probe of claim 29 wherein at least one of said third wave source and detector is disposed in a substantially middle portion of said symmetric scanning unit.

31. The optical probe of claim 1 wherein at least two of said symmetric scanning units are arranged symmetrically with respect to a global axis of symmetry.

32. The optical probe of claim 31 wherein at least one of said symmetric scanning units is disposed immediately below the other of said symmetric scanning units.

33. The optical probe of claim 31 wherein at least two of said symmetric scanning units are substantially laterally arranged.

34. The optical probe of claim 1 wherein at least two of said symmetric scanning units are arranged symmetrically with respect to a global point of symmetry.

35. The optical probe of claim 34 wherein at least two of said symmetric scanning units are arranged substantially arcuately around said point of symmetry.

36. The optical probe of claim 34 wherein at least two of said symmetric scanning units are arranged substantially concentrically around said point of symmetry.

37. The optical probe of claim 1 wherein at least one of said wave sources is configured to irradiate multiple sets of electromagnetic waves having different wave characteristics.

38. The optical probe of claim 1 wherein at least one of said wave detectors is configured to detect a plurality of sets of electromagnetic waves having different wave characteristics.

39. The optical probe of claim 1 wherein one of said wave sources is arranged to irradiate electromagnetic waves while at least one of said wave sources is not irradiating electromagnetic waves.

40. The optical probe of claim 1 wherein said electromagnetic waves are at least one of sound waves, near-infrared rays, infrared rays, visible lights, ultraviolet rays, lasers, and photons.

41. The optical probe of claim 1 wherein said images represent at least one of two-dimensional and three-dimensional distribution of at least one of said hemoglobins and said properties thereof.

42. The optical probe of claim 1 wherein said properties represent at least one of spatial distribution and temporal variation in at least one of said hemoglobins and said properties thereof.

43. The optical probe of claim 1 wherein said properties are at least one of absolute values and relative values of at least one of said hemoglobins and said properties thereof.

44. The optical probe of claim 1 wherein said properties include at least one of concentration of deoxygenated hemoglobin, concentration of oxygenated hemoglobin, and an oxygen saturation which is a ratio of said concentration of said oxygenated hemoglobin to a sum of said concentrations of said oxygenated hemoglobin and said deoxygenated hemoglobin.

45. The optical probe of claim 1 wherein said properties are extensive properties including at least one of volume, mass, weight, volumetric flow rate, and mass flow rate of said hemoglobins.

46. An optical probe of an optical imaging system capable of generating images representing distribution of hemoglobins or their properties in target areas of a physiological medium, said optical probe including a plurality of wave sources and a plurality of wave detectors, said wave sources configured to form optical coupling with said medium and to irradiate near-infrared electromagnetic waves thereinto and said wave detectors configured to detect said near-infrared electromagnetic waves and configured to generate output signals in response thereto, said optical probe comprising:

four symmetric scanning units wherein a first scanning unit is identical to a fourth scanning unit and wherein a second scanning unit is identical to a third scanning unit, each of said symmetric scanning units including a first wave source, a second wave source, a first wave detector, and a second wave detector, wherein said first wave source is disposed closer to said first wave detector than said second wave detector and wherein said second wave source is disposed closer to said second wave detector than said first wave detector, wherein a first near-distance between said first wave source and first wave detector is arranged to be substantially similar to a second near-distance between said second wave source and second wave detector, wherein a first far-distance between said first wave source and second wave detector is arranged to be substantially similar to a second far-distance between said second wave source and first wave detector, and wherein said first and second wave sources are configured to be synchronized with said first and second wave detectors to generate said output signals which represent optical interaction of said near-infrared waves with said hemoglobins in said target areas of said medium.

47. The optical probe of claim 46 wherein all of said wave sources and all of said wave detectors of each of said scanning units are substantially linearly disposed.

48. The optical probe of claim 47 wherein said first and second wave sources are interposed between said first and second wave detectors in said first and fourth scanning units and wherein said first and second wave detectors are interposed between said first and second wave sources in said second and third scanning units.

49. An optical probe of an optical imaging system capable of generating images representing distribution of hemoglobins or their properties in target areas of a physiological medium, said optical probe including a plurality of wave sources and a plurality of wave detectors, said wave sources configured to form optical coupling with said medium and to irradiate near-infrared electromagnetic waves thereinto and said wave detectors configured to detect said near-infrared electromagnetic waves and configured to generate output signals in response thereto, said optical probe comprising:

a plurality of wave sources; and a plurality of wave detectors, wherein at least one first wave source and at least one first wave detector define a first scanning element in which said first wave source irradiates said near-infrared electromagnetic waves and said first wave detector detects said waves irradiated by said first wave detector and generates a first output signal, wherein at least one second wave source and at least one second wave detector define a second scanning element in which said second wave source irradiates said near-infrared electromagnetic waves and said second wave detector detects said waves irradiated by said second wave detector and generates a second output signal, wherein said first and second scanning elements define a scanning unit in which said first and second wave sources are symmetrically disposed with respect to one of a line of symmetry and a point of symmetry and in each of which said first and second wave detectors are also symmetrically disposed with respect to one of said line of symmetry and said point of symmetry.

50. The optical probe of claim 49 wherein said first and second scanning units are configured to intersect each other.

51. The optical probe of claim 49 further comprising:

an imaging member configured to receive said first and second output signals generated by said first and second wave detectors, to obtain a set of solutions of a plurality of wave equations applied to said first and second wave sources and to said first and second wave detectors, to determine said distribution of at least one of hemoglobins and properties thereof, and to generate said images of said distribution.

52. The optical probe of claim 51 wherein said images are generated in an image domain, wherein said images are comprised of a plurality of voxels, wherein each of said first and second scanning units generates a plurality of first voxels and a plurality of second voxels, respectively, and wherein said imaging member is configured to calculate at least one first voxel value for each of said first voxels from said set of said solutions and at least one second voxel value for each of said second voxels from said set of said solutions.

53. The optical probe of claim 52 wherein said imaging member is configured to define a plurality of cross-voxels each of which is defined as an overlapping portion of said first and second voxels intersecting each other.

54. The optical probe of claim 53 wherein said imaging member is configured to calculate at least one cross-voxel value for each of said cross-voxels directly from said first and second voxel values of said intersecting first and second voxels, respectively.

55. The optical probe of claim 54 wherein each of said cross-voxel values is at least one of an arithmetic sum and arithmetic average of said first and second voxel values of said first and second voxels intersecting each other.

56. The optical probe of claim 54 wherein each of said cross-voxel values is at least one of a weighted sum and weighted average of said first and second voxel values of said first and second voxels intersecting each other.

57. A method for generating two-dimensional or three-dimensional images of a target area of a physiological medium by an optical imaging system with an optical probe, said images representing spatial or temporal distribution of hemoglobins or their properties in said medium, wherein said optical probe includes a plurality of wave sources and a plurality of wave detectors, said wave sources configured to form optical coupling with said target area of said medium and to irradiate near-infrared electromagnetic waves thereinto, said wave detector configured to form optical coupling with said target area of said medium and to generate output signals in response to said near-infrared electromagnetic waves detected thereby, said image generating method comprising the steps of:

providing a plurality of scanning elements each of which includes at least one of said wave sources for irradiating said waves and at least one of said wave detectors for detecting said waves irradiated by said at least one of said wave sources of said each of said scanning unit;

defining a plurality of scanning units each of which includes at least two of said scanning elements and, therefore, each of which includes at least two of said wave sources and at least two of said wave detectors;

scanning said target area by irradiating electromagnetic waves thereinto by said wave sources and by generating said output signals therefrom by said wave detectors;

grouping output signals generated by each of said scanning units;

obtaining a set of solutions of wave equations applied to said wave sources and detectors of each of said scanning units;

determining said distribution of at least one of hemoglobins and properties thereof from said set of solutions; and providing said images of said distribution.

58. The method of claim 57 further comprising:
scanning said target area over time;
determining said distribution of at least one of hemoglobins and properties thereof in said target area of said medium over time;
providing said images of said distribution over time; and
providing said images of changes in said distribution over time.

59. The method of claim 57 further comprising:
defining a plurality of first voxels in at least one of said scanning units;
determining at least one first voxel value for each of said first voxels, each of said first voxel values representing an average value of at least one of said hemoglobins and said properties thereof; and
generating said images of said distribution directly from said first voxel values.

60. The method of claim 59 wherein said defining comprises:

controlling resolution of said images by adjusting at lease one characteristic dimension of each of said first voxels.

61. The method of claim 60 wherein said controlling comprises at least one of:
adjusting at least one distance between at least one of said wave sources and at least one of said wave detectors of at least one of the same scanning element and the same scanning unit;
adjusting geometric arrangement between at least one of said wave sources and at least one of said wave detectors of at least one of the same scanning element and the same scanning unit;
adjusting geometric arrangement between at least two scanning elements of the same scanning unit;
adjusting geometric arrangement between at least two scanning units; and
adjusting data sampling rate of said output signals.

62. The method of claim 59 further comprising:
defining a plurality of second voxels in at least one of said scanning units;
determining at least one second voxel value for each of said second voxels, each second voxel value representing an average value of at least one of said hemoglobins and said properties thereof; and
generating said images of said distribution directly from said first and second voxel values.

63. The method of claim 62 further comprising:
defining a plurality of cross-voxels in at least one of said scanning units, each of said cross-voxels defined as an overlapping portion of two intersecting first and second voxels;
determining at least one cross-voxel value for each of said cross-voxels, each cross-voxel value representing an average value of at least one of said hemoglobins and said properties thereof; and generating said images of said distribution directly from said cross-voxel values and at least one of said first and second voxel values.

64. The method of claim 63 wherein said cross-voxel values are determined by at least one of:
adding said first and second voxel values of said intersecting first and second voxels;
arithmetically averaging said first and second voxel values of said intersecting first and second voxels;
adding weighted first and second voxel values of said intersecting first and second voxels; and
weight-averaging said first and second voxel values of said intersecting first and second voxels.

65. The method of claim 62 further comprising:
defining a plurality of third voxels in at least one of said scanning units;
determining at least one third voxel value for each of said third voxels, each third voxel value representing an average value of at least one of said hemoglobins and said properties thereof;
generating said images of said distribution directly from said first, second, and third voxel values.

66. The method of claim 65 further comprising:
defining a plurality of second cross-voxels in at least one of said scanning units, each of said second cross-voxels defined as an overlapping portion of two intersecting first and third voxels;
determining at least one second cross-voxel value for each of said second cross-voxels, each second cross-voxel value representing an average value of at least one of said hemoglobins and said properties thereof; and generating said images of said distribution based on at least one of said cross-voxel values, second cross-voxel values, first voxel values, second voxel values, and third voxel values.

* * * * *